(12) United States Patent
Yamashita

(10) Patent No.: US 8,702,783 B2
(45) Date of Patent: Apr. 22, 2014

(54) STENT DELIVERY SYSTEM

(75) Inventor: Hideaki Yamashita, Shizuoka (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 219 days.

(21) Appl. No.: 13/208,866

(22) Filed: Aug. 12, 2011

(65) Prior Publication Data

US 2012/0022635 A1 Jan. 26, 2012

Related U.S. Application Data

(63) Continuation of application No. PCT/JP2010/052085, filed on Feb. 12, 2010.

(30) Foreign Application Priority Data

Feb. 16, 2009 (JP) .................................. 2009-033280

(51) Int. Cl.
*A61F 2/06* (2013.01)

(52) U.S. Cl.
USPC ......................................................... 623/1.11

(58) Field of Classification Search
USPC ............................................... 623/1.11–1.12
See application file for complete search history.

(56) References Cited

U.S. PATENT DOCUMENTS

| | | | | |
|---|---|---|---|---|
| 3,777,591 A | * | 12/1973 | Thomasian | ...................... 74/576 |
| 8,366,760 B2 | * | 2/2013 | Kumoyama | .................. 623/1.11 |
| 2006/0259124 A1 | * | 11/2006 | Matsuoka et al. | ........... 623/1.12 |
| 2010/0076541 A1 | | 3/2010 | Kumoyama | |

FOREIGN PATENT DOCUMENTS

| | | |
|---|---|---|
| JP | 2007-097620 A | 4/2007 |
| JP | 2008-086465 A | 4/2008 |
| WO | WO 2006/104143 A1 | 10/2006 |
| WO | WO 2008/136329 A1 | 11/2008 |

OTHER PUBLICATIONS

International Search Report (PCT/ISA/210) issued on May 25, 2010, by Japanese Patent Office as the International Searching Authority for International Application No. PCT/JP2010/052085.
Extended European Search Report dated Oct. 31, 2012, issued by the European Patent Office in corresponding European Patent Application No. 107412942 (6 pages).
Official Action issued Jul. 31, 2013 by the State Intellectual Property Office of P.R. China in Chinese Patent Application No. 201080003850.7 and English language translation (11 pgs).

* cited by examiner

*Primary Examiner* — Darwin Erezo
*Assistant Examiner* — Martin Ton
(74) *Attorney, Agent, or Firm* — Buchanan Ingersoll & Rooney PC

(57) ABSTRACT

A stent delivery system includes: a distal-side tube; a proximal-side tube; a tubular member which contains a stent; a wire which has one end fixed to the tubular member; and an operating section which has a wire winding mechanism and a wire winding amount restriction mechanism for restricting the length of wire which is pulled. The operating section has an operating rotary roller; a winding shaft section and driving gear which are provided coaxially and integrally with the roller; and a driven gear which is intermittently rotated by the driving gear. The driving gear and the driven gear have the stopper function by which rotation of the driving gear is stopped after the driving gear is rotated a predetermined amount.

19 Claims, 15 Drawing Sheets

STENT DELIVERY SYSTEM

This application is a continuation of International Application No. PCT/JP2010/052085 filed on Feb. 12, 2010, and claims priority to Japanese Application No. 2009-033280 filed on Feb. 16, 2009, the entire content of both of which is incorporated herein by reference.

TECHNICAL FIELD

The present invention relates to a stent delivery system for putting a stent indwelling in a stenosed part or occluded part in a living body such as a blood vessel, a bile duct, a trachea, an esophagus, an urethra, a digestive tract, or other type of organ.

BACKGROUND DISCUSSION

Conventionally, there have been proposed stent delivery systems for putting a stent indwelling in a stenosed part or occluded part in a living body lumen or a body cavity such as a blood vessel, a bile duct, an esophagus, a trachea, an urethra, a digestive tract or the like organ so as to secure or maintain a lumen or body cavity space.

The stents delivered by the above-mentioned stent delivery systems are classified, by the function or the method of putting the stent indwelling, into balloon-expandable stents and self-expanding stents.

The balloon-expandable stent is a stent which itself does not have an expanding function. In order to put such a stent indwelling in a target part, for example, the stent mounted on a balloon is inserted into the target part, and thereafter expansion (plastic deformation) of the stent is effected by a dilating force of the balloon, whereby the stent is put into close contact with an inner surface of the target part and fixed in situ.

This type of stent requires a stent-expanding operation as discussed above, but it has little difficulty being put in an indwelling state, because the stent can be mounted directly on the contracted balloon and put indwelling in the target part.

On the other hand, the self-expanding stent is a stent which itself has contracting and expanding functions. In order to put this stent indwelling in a target part, the stent in the contracted state is inserted into the target part, and thereafter the stress loaded for maintaining the contracted state is removed. For instance, the stent is contained in its contracted state in a sheath having an outside diameter smaller than the inside diameter of the target part, the distal end of the sheath is brought to the target part, and thereafter the stent is pushed out of the sheath. The stent thus pushed out is released from the sheath, whereby the stress applied to the stent is removed, so that the stent expands and is restored to its shape before contraction. As a result, the stent is put in close contact with the inner surface of the target part and fixed in situ.

This type of stent is a stent which itself has an expanding force, and, therefore, does not need a stent-expanding operation, unlike balloon-expandable stents. This type of stent does not suffer from the difficulty that a reduction in diameter is induced by the pressure of a blood vessel or the like, leading to restenosis.

However, self-expanding stents are generally said to be more difficult to accurately put indwelling, than balloon-expandable stents. The reason is as follows. In the case of a balloon-expandable stent, after the stent is placed in a target stenosis part, it is necessary to inject a liquid into the balloon to expand and position the stent. Therefore, the stent does not move distally or proximally at the time of expansion. On the other hand, a delivery system for a self-expanding stent is constructed so that the stent is restrained by containing it between an inner tube and an outer tube, a lock section for restricting movement of the stent is provided on the stent proximal side of the inner tube, and the outer tube is pulled toward the proximal side, whereby the stent is released from being restrained and is permitted to self-expand. In this case, the stent is said to be liable to move distally at the time of expansion, due to loosening of the outer tube in a body cavity, friction between the outer tube and the body cavity or a catheter in which the outer tube is introduced, or friction between the outer tube and a valve of a device called introducer for introducing the system into a living body.

In view of the foregoing, the present applicant proposed a system shown in Japanese Application Publication No. 2007-97620 which corresponds to U.S. Application Publication No. 2006/0259124.

This stent delivery system 1 includes a distal-side tube 2 having a guide wire lumen 21, a proximal-side tube 4 fixed to a proximal section of the distal-side tube 2, a stent-containing tubular member 5 which envelops the distal side of the distal-side tube 2 and which is slidable in the proximal direction, a stent 3 contained in the tubular member 5, and a wire 6 for moving the tubular member 5 toward the proximal side. The distal-side tube 2 has a proximal-side opening 23 opening on the proximal side of the distal-side tube 2, a stent lock section 22 for restricting movement of the stent toward the proximal side, and an operating section equipped with a wire winding mechanism and a wire winding amount restriction mechanism. This stent delivery system has a merit in that it is free of generation of needless curving or damage of a catheter due to excessive winding of the wire for pulling toward the proximal side the tubular member 5 serving as a restraint body for the stent.

The system disclosed in the above-cited application publication is sufficiently effective in that the wire winding mechanism is composed of an operating rotary roller, and a winding shaft section rotated by the rotation of the roller. In addition, the wire winding amount restriction mechanism is composed of a winding restricting linear body of a predetermined length and having one end gripped by an operating section, and the other end fixed to a winding shaft section of the operating rotary roller or to a linear body winding shaft section provided separately from the winding shaft section. By rotating the operating rotary roller in a wire winding direction, the linear body is wound onto the linear body winding shaft section by a predetermined amount, whereon further winding is impossible. In this stent delivery system, however, both the wire and the winding restricting linear body are wound by the rotation of the operating rotary roller, so that rotational resistance on the operating rotary roller cannot be lowered. In addition, the above-mentioned application publication discloses an embodiment wherein the wire winding amount restriction mechanism is composed of a projected section provided on the operating rotary roller, and a lock section which is provided inside the operating section and makes contact with the operating rotary roller, after rotation of the operating rotary roller by a predetermined amount in a wire winding direction, so as to restrict further rotation of the operating rotary roller. In the system according to this embodiment, however, the operating rotary roller can be set only to a rotating amount of less than one revolution, so that the wire winding amount which can be restricted by the wire winding amount restriction mechanism is small.

SUMMARY

The stent delivery system disclosed here includes: a tube body having a guide wire lumen; a stent-containing tubular member enveloping a distal end portion of the tube body and being slidable relative to the tube body toward a proximal end of the tube body; a stent contained in the stent-containing tubular member; a wire having one end portion fixed to the stent-containing tubular member and operable to move the stent-containing tubular member in a proximal direction; and wherein the tube body includes a stent lock section abutting a proximal end of the stent contained in the stent-containing tubular member to restrict movement of the stent in the proximal direction. The stent possesses a cylindrical shape and is contained in the stent-containing tubular member while in a compressed state in which the stent is compressed toward a center axis of the stent, and the stent is restored to a pre-compression shape through outward expansion when indwelled in a living body. The stent delivery system also includes an operating section located proximally of the stent-containing tubular member, wherein the operating section includes a wire winding mechanism for winding the wire to thereby move the stent-containing tubular member toward the proximal direction and a wire winding amount restriction mechanism for restricting a length of the wire pulled by the wire winding mechanism, and wherein the wire winding mechanism includes an operating section housing and an operating rotary roller having a portion exposed from the operating section housing which is operable by a user to rotate the operating rotary roller and wind the wire. The wire winding mechanism includes a winding shaft section coaxial and integral with the operating rotary roller, the one end portion of the wire is held on the winding shaft section, and wherein the winding shaft section has a smaller outer diameter than the operating rotary roller, and the wire winding amount restriction mechanism includes a driving gear coaxial and integral with the operating rotary roller and a driven gear rotated intermittently by the driving gear, with the driven gear and the driving gear being configured as a stopper to stop rotation of the driving gear after rotation of the driving gear by a predetermined amount.

In the stent delivery system disclosed here, therefore, the stopper is operated after a sufficient amount of wire is wound. An increase in the rotational resistance on the operating rotary roller due to the wire winding amount restriction mechanism and the stopper function is extremely little, so that operationality of the operating rotary roller is favorable. In the stent delivery system disclosed here, the wire winding amount restriction mechanism is provided, whereby it is ensured that there is no possibility of generation of needless curving or damage of a catheter due to excessive winding of the wire by which the tubular member serving as a restraint body for the stent is pulled toward the proximal side.

The stent delivery system disclosed here has an operating section which functions after winding of a wire by a sufficient amount and which permits excellent wire winding by an operating rotary roller, without any increase in the rotational resistance on the operating rotary roller.

The driven gear can be configured to include a plurality of turning grooves extending a predetermined length in the direction of a rotary shaft and with one stopping recess, with the turning grooves and the stopping recess arranged at approximately equal intervals around the rotary shaft, and the driving gear is provided with a driven gear turning projection configured to enter into and be disengaged from the turning grooves and engageable with the stopping recess.

The stopping recess is a recess which does not have a portion extending a predetermined length in the direction of the rotary shaft (i.e., the stopping recess is shallower than the turning grooves).

The outer edges of the driven gear between the plurality of turning grooves and the stopping recess are arcuate recesses, and the driving gear has a circular or arcuate rib having an outer edge shape corresponding to each of the arcuate recesses of the driven gear.

The driving gear is preferably configured so that in the vicinity of the driven gear turning projection, includes a rib-missing section where the circular or arcuate rib is absent.

The driving gear is preferably provided at a surface, on the opposite side to the winding shaft section, of the rotary roller. The operating section includes the operating rotary roller having the winding shaft section and the driving gear and the operating section housing for containing the driven gear, wherein the operating section housing has a shaft-forming projection to be a rotary shaft for the driven gear, and the driven gear has a bearing section for receiving the shaft-forming projection.

The operating section housing is preferably provided, in an inner surface of the housing, with a recess for containing the driven gear and the projection of the driving gear. Also, the driven gear and a driven gear containing section of the operating section housing are each preferably provided with a driven gear initial state setting through-hole. The driving gear is preferably smaller than the operating rotary roller in diameter.

The operating section preferably includes a lock mechanism for unlockably locking rotation of the wire winding mechanism, and the operating section preferably has a reverse rotation restriction mechanism for restricting rotation of the wire winding mechanism in a reverse direction relative to a winding direction for the wire.

The wire winding mechanism includes the winding shaft section, and a collar section which envelops the winding shaft section, forms an annular space between itself and an outer surface of the winding shaft section, and restrains the wire wound onto the winding shaft section from loosening. And the driving gear and the driven gear preferably constitute a Geneva gear mechanism.

The tube body can be configured to include a distal-side tube having a guide wire lumen, and a proximal-side tube having a distal portion fixed to a proximal portion of the distal-side tube, with the stent-containing tubular member surrounding or enveloping a distal side of the distal-side tube and being slidable toward the proximal end of the distal-side tube, and with the wire extending inside the proximal-side tube, and the distal-side tube having the stent lock section.

The stent delivery system can also include a fixed tube to which a proximal portion of the distal-side tube and a distal portion of the proximal-side tube are fixed and which has an opening communicating with the guide wire lumen. Additionally, the stent delivery system preferably includes a slide tube disposed so as to be close to a proximal end of the stent-containing tubular member, with the fixed tube being so formed that it can contain the slide tube from the proximal side or the slide tube can be covered from the proximal side, and with the slide tube can being slidable toward the proximal side together with the stent-containing tubular member by pulling of the wire and is not fixed to the stent-containing tubular member. Preferably, the slide tube includes a slide tube body, and a distal-side tubular member which is fixed to a distal portion of the slide tube body, covers a distal end of the slide tube body, and extends from the distal end of the slide tube body toward the distal end of the stent delivery system, and the distal-side tubular member is an integrally molded tubular body having a reduced-diameter section which is located between a distal end and a proximal end of the distal-side tubular member and is reduced at least in inside diameter.

According to another aspect, the stent delivery system comprises: a tube body having a guide wire lumen for receiving a guide wire to guide movement of the stent delivery system; a stent-containing tubular member surrounding a portion of the tube body and axially movable relative to the tube body; a compressed stent positioned in the stent-containing tubular member, with the compressed stent expanding to a non-compressed state when removed from the stent-containing tubular member and indwelled in a living body; a wire having one end portion fixed to the stent-containing tubular member; a rotary roller rotatably mounted in a housing and rotatably operable from outside the housing to rotate the operating rotary roller; and a winding shaft coaxial with the rotary roller and fixed to the rotary roller to rotate together with the rotary roller, the opposite end portion of the wire being held on the winding shaft so that the wire is wound on the winding shaft during rotation of the rotary roller in one rotational direction to move the stent-containing tubular member proximally to allow the stent to be removed from the stent-containing tubular member. A driving gear is coaxial and integral with the rotary roller to rotate with the rotary roller about a first rotation axis, wherein the driving gear includes an engaging portion which rotates together with the driving gear, and a driven gear is positioned adjacent the driving gear and rotatable about a second rotation axis non-coaxially arranged relative to the first rotation axis. The engaging portion of the driving gear engages the driven gear during rotation of the driving gear to cause the driven gear to rotate, and the driven gear includes a stop portion engageable by the engaging portion of the driving gear after the driving gear has rotated a predetermined amount so that further rotation of the driving gear is stopped when the engaging portion engages the stop. The predetermined amount of rotation of the driving gear is an amount that winds a portion of the wire on the winding shaft so that the stent-containing tubular member is moved proximally to allow the stent to be removed from the stent-containing tubular member.

BRIEF DESCRIPTION OF THE DRAWING FIGURES

DETAILED DESCRIPTION

Figure 1:
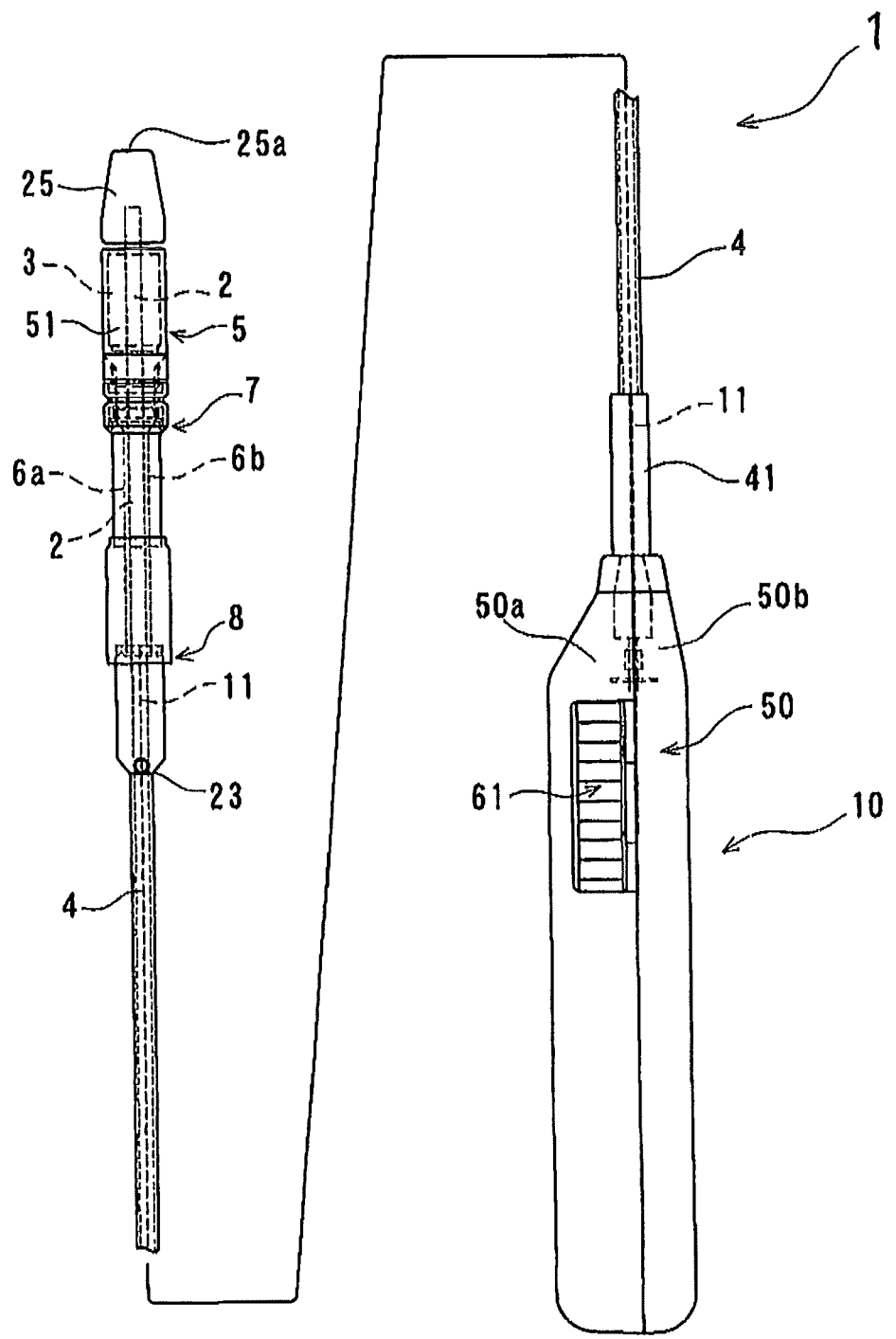
FIG. 1 is a front view of a stent delivery system according to an embodiment disclosed here by way of example.

Set forth below is a description of a stent delivery system 1 disclosed here in terms of one embodiment disclosed by way of example. The stent delivery system includes a tube body having a guide wire lumen 21, a stent-containing tubular member which envelops a distal end of the tube body and which is slidable toward the proximal end of the tube body, a stent 3 contained in the stent-containing tubular member 5, and a wire 6 (6*a*, 6*b*) having one end portion fixed to the stent-containing tubular member 5 for moving the stent-containing tubular member 5 toward the proximal end by pulling toward the proximal end of the tube body.

Specifically, the tube body includes a distal-side tube 2 having a guide wire lumen, and a proximal-side tube 4 having a distal portion fixed to a proximal portion of the distal-side tube 2. The stent-containing tubular member 5 envelops a portion of the distal end of the distal-side tube 2 and is slidable toward the proximal end of the distal-side tube 2. In the illustrated embodiment, the distal end portion of the distal-side tube 2 extends distally beyond the distal-most end of the stent-containing tubular member 5. The wire 6 (6*a*, 6*b*) extends inside the proximal-side tube 4. The distal-side tube 2 has a stent lock section 22.

Thus, the stent delivery system 1 in the embodiment shown in the drawings includes the distal-side tube 2 having the guide wire lumen 21 and the proximal-side tube 4, a fixed tube 8 to which a proximal portion of the distal-side tube 2 and a distal portion of the proximal-side tube 4 are fixed and which has an opening 23 communicating with the guide wire lumen 21, the stent-containing tubular member 5 which envelops the distal end of the distal-side tube 2 and is slidable toward the proximal end of the distal-side tube 2, the stent 3 contained in the stent-containing tubular member 5, and the wire 6 (6a, 6b) of which one end portion is fixed to the stent-containing tubular member 5, which extends inside the proximal-side tube 4 and which constitutes moving means for moving the stent-containing tubular member 5 toward the proximal end by pulling or applying a force toward the proximal end of the proximal-side tube.

In addition, the distal-side tube 2 has a stent proximal portion lock section 22 which is located on the distal end, which makes contact with the proximal end of the stent 3 contained in the stent-containing tubular member 5, and which restricts movement of the stent 3 toward the proximal end.

The stent 3 is cylindrically shaped (inclusive of substantially cylindrically shaped), is contained in the stent-containing tubular member 5 while being compressed toward its center axis, and, upon being discharged from the stent-containing tubular member 5, expands outward to restore its pre-compression shape.

At the proximal portion of the proximal-side tube 4, there is provided an operating section 10 which has a wire winding mechanism for winding the wire 6 (6a, 6b) and thereby move the stent-containing tubular member 5 in the proximal direction and a wire winding amount restriction mechanism for restricting the length of the wire pulled by the wire winding mechanism (i.e., the amount by which the wire 6 (6a, 6b) is wound).

In addition, the wire winding mechanism has a winding shaft section 63 (see, for example, FIG. 15) which is coaxial and integral with an operating rotary roller 61. The winding shaft section 63 is smaller in diameter than the operating rotary roller 61, and holds proximal portions of the wires 6a, 6b. The wire winding amount restriction mechanism has a driving gear 12 (Geneva wheel) coaxial and integral with the operating rotary roller 61, and a driven gear 40 (Geneva cross) rotated intermittently by the driving gear 12, and, further, it has a stopper function for stopping rotation of the driving gear 12 after rotation of the driving gear 12 by a predetermined amount. The driving gear 12 (Geneva wheel) and the driven gear 40 (Geneva cross) constitute a Geneva gear mechanism.

The stent delivery system 1 according to this embodiment also includes a slide tube 7. In addition, the fixed tube 8 connects the distal-side tube 2 and the proximal-side tube 4 to each other, and has the opening 23 shown in FIGS. 1 and 2 communicating with a proximal portion of the distal-side tube 2.

The slide tube 7 is disposed close to the proximal end of the stent-containing tubular member 5. The fixed tube 8 is so formed that it can contain the slide tube 7 from the proximal end or the slide tube 7 can be covered from the proximal end. The slide tube 7 can be moved proximally toward the proximal end together with the stent-containing tubular member 5, by pulling the wire 6, and it is not fixed to the stent-containing tubular member 5. Further, the slide tube 7 includes a slide tube body 71, and a distal-side tubular member 72 which is fixed to the distal end of the slide tube body 71, which covers the distal end of the slide tube body 71 and which extends distally from the distal end of the slide tube body 71 toward the distal end of the stent delivery system 1.

In addition, the distal-side tubular member 72 is an integrally molded, one-piece unitarily formed tubular body having a reduced-diameter section 73 between the distal end and the proximal end of the distal-side tubular member 72 and which is reduced at least in inside diameter.

In the stent delivery system 1 in this embodiment, the outside diameter of the proximal-side tube 4 is smaller than the outside diameter of that section of the stent delivery system 1 which has the maximum diameter on the distal side of the proximal-side tube 4. Consequently, even in the condition where the guide wire extending to the proximal side from the opening 23 is laid along a side surface of the proximal-side tube, the maximum outside diameter of the stent delivery system can be made to be comparable to the outside diameter of that section of the stent delivery system which has the maximum diameter on the distal side relative to the proximal-side tube. Accordingly, the stent delivery system can be inserted into a relatively small-diameter blood vessel.

Figure 2:
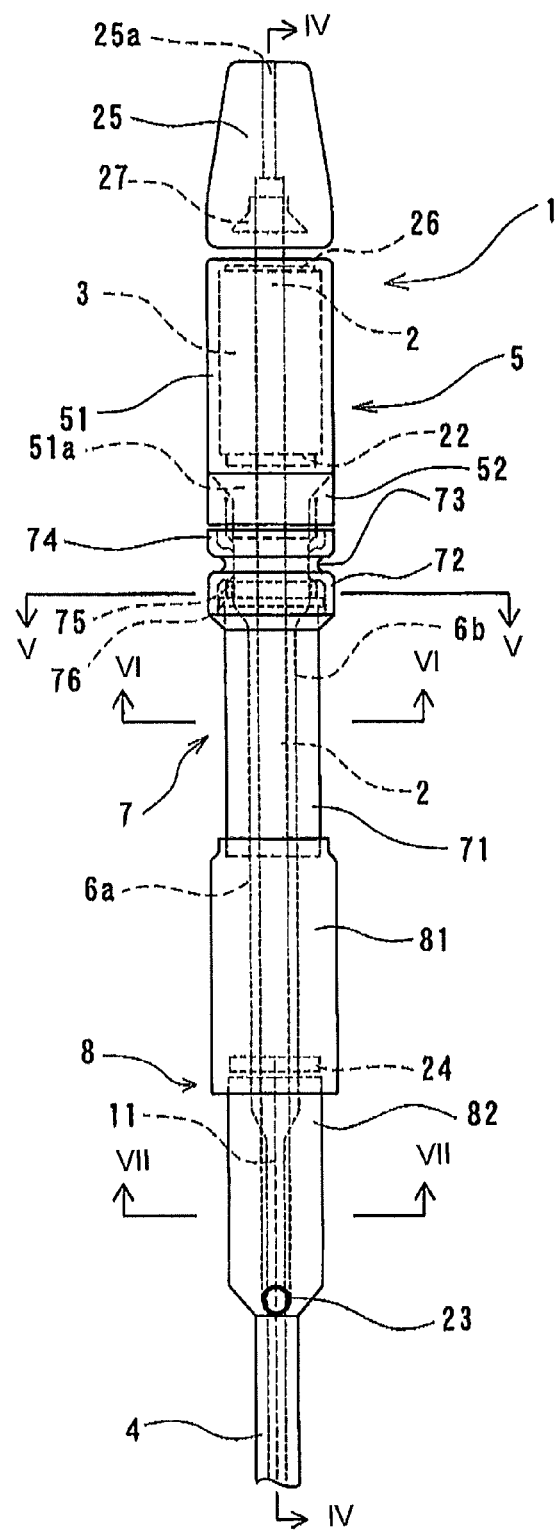
FIG. 2 is an enlarged front view of a distal portion of the stent delivery system of FIG. 1.
Figure 3:
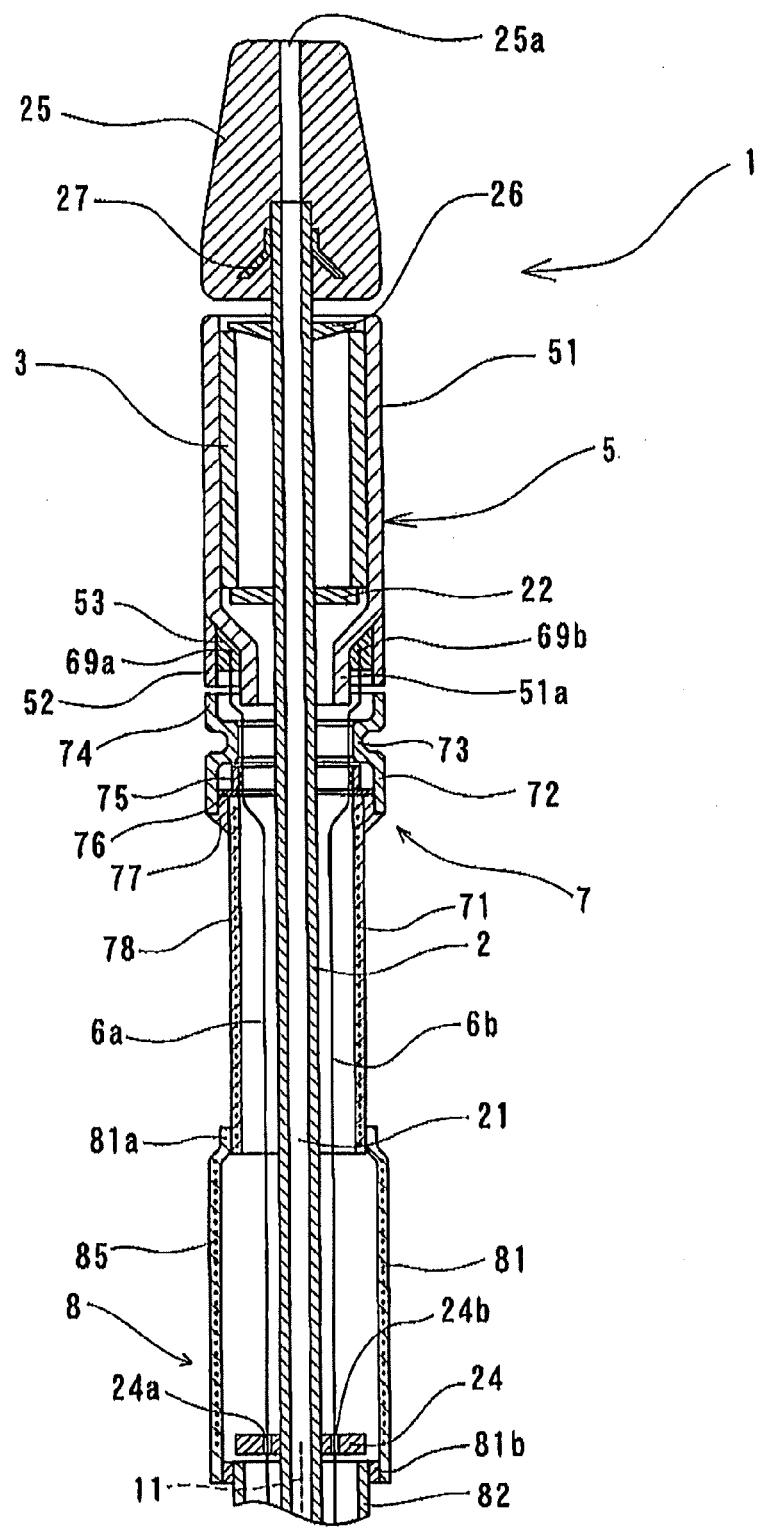
FIG. 3 is an enlarged longitudinal cross-sectional view of the distal portion of the stent delivery system of FIG. 1.
Figure 4:
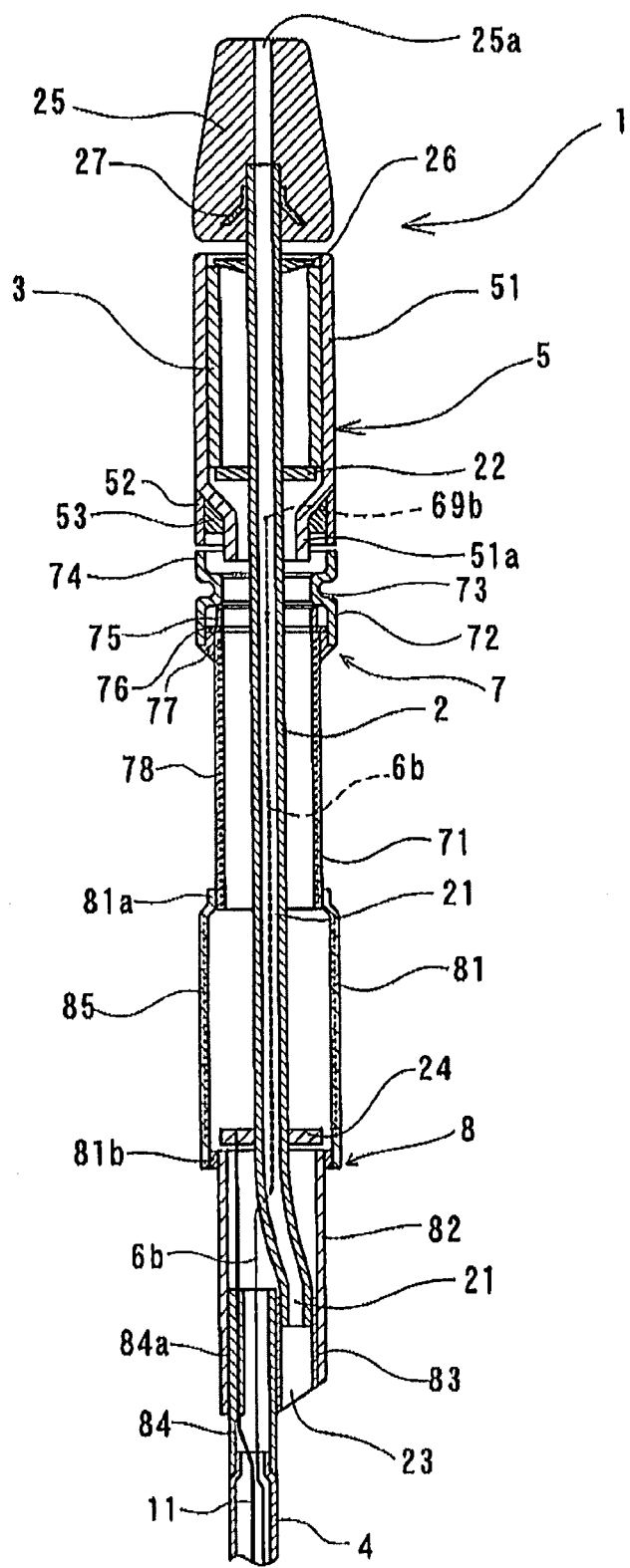
FIG. 4 is a cross-sectional view taken along the section line IV-IV of FIG. 2.
Figure 5:
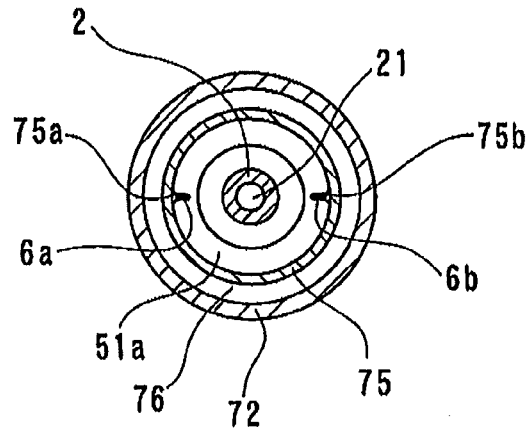
FIG. 5 is an enlarged cross-sectional view taken along the section line V-V of FIG. 2.
Figure 6:
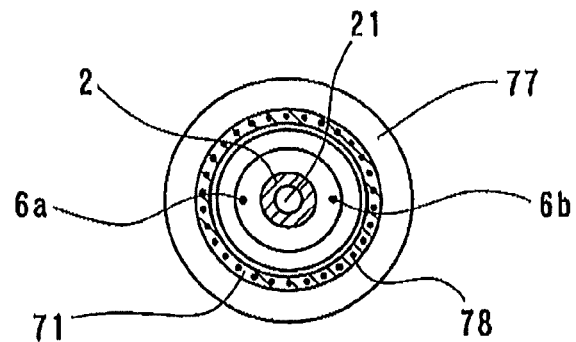
FIG. 6 is an enlarged cross-sectional view taken along the section line VI-VI of FIG. 2.

As shown in FIGS. 1 to 10, the distal-side tube 2 is a tube body which has a guide wire lumen 21 penetrating therethrough from the distal end to the proximal end thereof. A distal portion of the distal-side tube 2 includes a distal member 25 fixed to the distal end of the distal-side tube 2, and the distal member 25 includes a distal opening 25a at the distal end thereof. The distal portion (i.e., the distal member 25) may be formed integrally with the distal-side tube. In addition, the distal-side tube 2 is fixed to the fixed tube 8 at a proximal portion thereof. The proximal end of the distal-side tube 2 communicates with the opening 23 provided in the fixed tube 8 as shown in FIG. 4. In addition, a proximal portion of the distal-side tube 2 is curved, as shown in FIG. 4. The opening 23 is formed in a slanting manner so as to be inclined toward the proximal side, as shown in FIGS. 1 and 4. This permits relatively easy guiding of the guide wire.

As shown in the drawings, the distal-side tube 2 is a tube body through which passes the guide wire lumen 21 which extends from the distal end of the distal-side tube 2 to the proximal end of the distal-side tube 2. The distal-side tube 2 has an outside diameter of 0.3 to 2.0 mm, preferably 0.5 to 1.5 mm, an inside diameter of 0.2 to 1.5 mm, preferably 0.3 to 1.2 mm, and a length of 20 to 600 mm, preferably 30 to 450 mm.

In addition, the distal member 25 is located on the distal side relative to the distal end of the stent-containing tubular member 5 (i.e., the distal member extends distally beyond the distal-most end of the distal-side tube 2), and preferably possesses a tapered shape such as to gradually decrease in outer diameter in the distal direction as shown in FIGS. 1 to 4. Formation in such a shape permits relatively easy insertion of the stent delivery system into a stenosed part. The distal-side tube 2 also preferably includes a stopper which is provided on the distal side relative to the stent 3 and which inhibits the stent-containing tubular member from moving in the distal direction. In this embodiment, the proximal end face of the distal member 25 can abut the distal end face of the stent-containing tubular member 5, and functions as the above-mentioned stopper.

The outside diameter of the distal-most portion of the distal member (distal portion) 25 is preferably 0.5 to 1.8 mm. In addition, the outside diameter of the maximum-diameter section of the distal member (distal portion) 25 is preferably 0.8 to 4.0 mm. Further, the length of the distal-side tapered section is preferably 2.0 to 20.0 mm.

As shown in FIGS. 3 and 4, the distal-side tube 2 has the stent proximal portion lock section 22 provided at a position a predetermined distance in the proximal direction from the distal end of the tube 2, for restricting movement of the stent 3 toward the proximal side. The lock section 22 is preferably an annular projected section. The distal side relative to the stent proximal portion lock section 22 is a stent-containing part. The outside diameter of the lock section 22 is so set as to permit the lock section 22 to abut on the proximal end of the stent 3 in its compressed state. In addition, even if the stent-containing tubular member 5 is moved toward the proximal side, the stent 3 is kept in its position by the lock section 22, so that the stent 3 is consequently discharged from the stent-containing tubular member 5.

In the stent delivery system 1 according to this embodiment, as shown in FIGS. 3 and 4, the distal-side tube 2 has a stent distal portion lock section 26 provided at a position a predetermined distance (roughly the axial length of the stent) in the distal direction from the stent proximal portion lock section 22. As shown in FIGS. 3 and 4, the stent distal portion lock section 26 is located slightly on the proximal side relative to the distal-most end of the stent-containing tubular member 5. The lock section 26 is preferably an annular projected section. In addition, the space between the stent distal portion lock section 26 and the stent proximal portion lock section 22 is a stent-containing part. The outside diameter of the lock section 26 is so set as to permit the lock section 26 to abut on the distal end of the stent 3 in its compressed state. The stent distal portion lock section 26 is preferably configured so that the proximal end surface is a tapered surface decreasing in outer diameter in the proximal direction. This helps ensure that, at the time of discharge (release) of the stent, the stent distal portion lock section 26 does not obstruct the operation, and that the recovery of the stent delivery system 1 after discharge (release) of the stent 3 (specifically, the containment of the stent delivery system 1 into a guiding catheter or a sheath) is facilitated.

The outside diameters of the stent proximal portion lock section 22 and the stent distal portion lock section 26 are preferably 0.8 to 4.0 mm. While the stent proximal portion lock section 22 and the stent distal portion lock section 26 are preferably annular projected sections as shown in the drawings, it is sufficient that these lock sections can restrict movement of the stent 3 and permit pushing-out thereof; for example, each of these lock sections may be one or more projections formed integrally with the distal-side tube 2 (rather than the illustrated lock sections which are annular members each extending around the entire circumference of the distal-side tube 2) or provided as members separate from the distal-side tube 2. In addition, the stent proximal portion lock section 22 and the stent distal portion lock section 26 may be composed of separate members formed from a radiopaque material. This ensures that the position of the stent can be accurately grasped under radioscopy, and facilitates procedures. Preferable examples of the radiopaque material include gold, platinum, platinum-iridium alloy, silver, stainless steel, platinum, and their alloys. The stent proximal portion lock section 22 and the stent distal portion lock section 26 are each mounted by a method in which a wire is formed from a radiopaque material and is wound around the outer surface of the distal-side tube, or a method in which a pipe is formed from a radiopaque material and is caulked or adhered.

The material forming the distal-side tube is preferably a material which has hardness and flexibility. Preferable examples of the material usable here include polyolefins such as polyethylene, polypropylene, etc., polyamides, polyesters such as polyethylene terephthalate, etc., fluoro polymers such as ETFE, etc., PEEK (polyether-ether ketone), and polyimides. Among the just-mentioned resins, particularly preferred are thermoplastic resins. Incidentally, an exposed surface of the distal-side tube may be coated with a resin which has bio-compatibility, particularly, antithrombotic properties. Preferable examples of the material usable as antithrombotic material include polyhydroxyethyl methacrylate, and hydroxyethyl methacrylate-styrene copolymers (for example, HEMA-St-HEMA block copolymer).

In addition, in the case where the distal portion is constituted of a member separate from the distal-side tube, the distal portion (distal member) 25 is preferably formed by use of a flexible material. Examples of the material to be used here include synthetic resin elastomers such as olefin elastomers (for example, polyethylene elastomer, polypropylene elastomer), polyamide elastomers, styrene elastomers (for example, styrene-butadiene-styrene copolymer, styrene-isoprene-styrene copolymer, styrene-ethylenebutylene-styrene copolymer), polyurethane, urethane elastomer, fluororesin elastomers, etc., and rubbers such as synthetic rubbers such as urethane rubber, silicone rubbers, butadiene rubber, etc., and natural rubbers such as latex rubber, etc.

In the stent delivery system 1 according to this embodiment disclosed by way of example, the distal-side tube 2 and the distal member 25 are composed of separate members, and the distal-side tube 2 has a stopper member 27 fixed to a distal portion. The stopper member 27 includes a tubular section fixed to the distal-side tube 2, and a skirt section spreading in a tapered form from the tubular section. In addition, the stopper member 27 is embedded in the distal member 25, thereby inhibiting or preventing the distal member 25 from being separated or moved toward the distal side. The stopper member 27 is preferably formed from a metal (for example, stainless steel).

As shown in FIGS. 1, 2 and 4, the proximal-side tube 4 is a tube body which is hollow throughout its length from the distal end to the proximal end, and has the operating section 10 fixed to the proximal end thereof. A distal portion of the proximal-side tube 4 is joined to the fixed tube 8 by a fixation member 84. The proximal-side tube 4 is provided therein with a wire lumen through which the wire 6 can be passed.

The proximal-side tube 4 has a length of 300 to 1500 mm, preferably 1000 to 1300 mm, an outside diameter of 0.5 to 1.5 mm, preferably 0.6 to 1.3 mm, and an inside diameter of 0.3 to 1.4 mm, preferably 0.5 to 1.2 mm.

The offset distance between the center axis of the proximal-side tube 4 and the center axis of the distal-side tube 2 is preferably 0.1 to 2.0 mm, particularly 0.5 to 1.5 mm.

The material forming the proximal-side tube is preferably a material which has hardness and flexibility. Preferable examples of the material usable here include polyolefins such as polyethylene, polypropylene, etc., nylons, polyethylene terephthalate, fluro polymers such as ETFE, etc., PEEK (polyether-ether ketone), and polyimides. Incidentally, an outer surface of the proximal-side tube may be coated with a resin which has bio-compatibility, particularly, antithrombotic properties. Examples of the material usable as antithrombotic material include polyhydroxyethyl methacrylate, and hydroxyethyl methacrylate-styrene copolymers (for example, HEMA-St-HEMA block copolymer). In addition, as the material for forming the proximal-side tube 4, there is preferably used a material which is comparatively high in rigidity. Examples of the usable material include metals such as Ni—Ti, brass, stainless steel, aluminum, etc. Further, there can also be used those resins which are comparatively high in rigidity, examples of which include polyimides, vinyl chloride, polycarbonate, etc.

Figure 10:
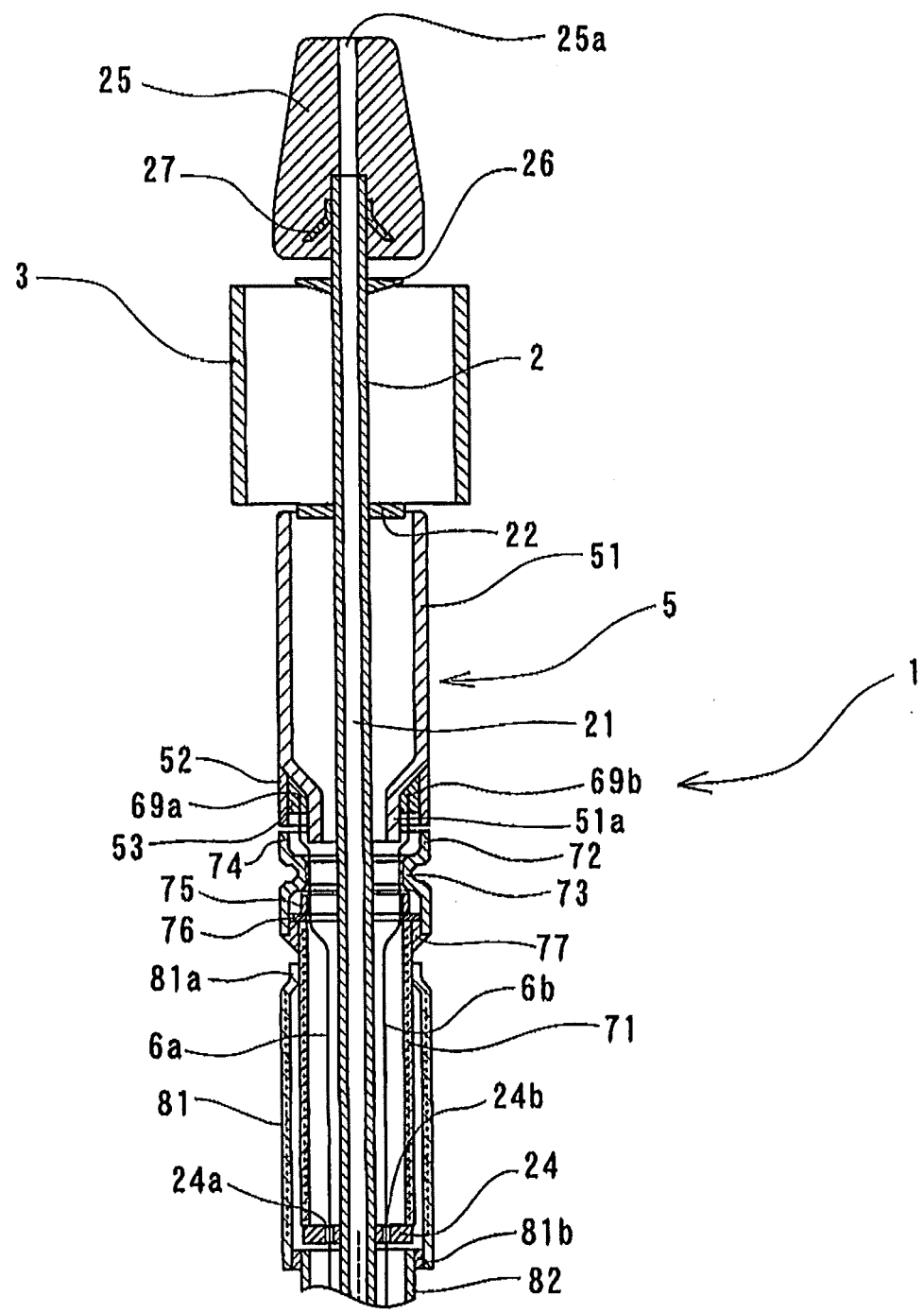
FIG. 10 is an illustration of operation of the stent delivery system according to this disclosed embodiment.

As shown in FIGS. 1 to 5 and 8, the stent-containing tubular member 5 is a tubular body having a predetermined length. It has openings (i.e., is open) at the distal end and the proximal end. The distal opening functions as a discharge (release) port for the stent 3 at the time of putting the stent 3 indwelling in a stenosed part in a body cavity. When pushed out via the distal opening, as shown in FIG. 10, the stress load (compression load) on the stent 3 is relieved and the stent is permitted to expand so that the stent 3 is restored to or returns to its pre-compression shape.

The stent-containing tubular member 5 has a length of preferably about 20 to 400 mm, particularly 30 to 300 mm. In addition, its outside diameter is preferably about 1.0 to 4.0 mm, particularly 1.5 to 3.0 mm. Besides, the inside diameter of the stent-containing tubular member 5 is preferably about 1.0 to 2.5 mm.

In addition, the stent-containing tubular member 5 includes a tubular member body section 51 having a small-diameter section 51a provided at a proximal portion thereof, and a tubular section 52 provided so as to envelop or surround the small-diameter section 51a. A proximal portion of the small-diameter section 51a extends proximally beyond the proximal-most end of the tubular section 52. Specifically, distal portions 69 (69a, 69b) of the wires 6 (6a, 6b) enter into a gap between the small-diameter section 51a and the tubular section 52, and are fixed to the stent-containing tubular member 5 by a fixing agent 53 filling the gap. The small-diameter section 51a includes a tapered section of which the outside diameter decreases in the proximal direction, and a short cylindrical section extending from the tapered section in the proximal direction. In addition, the tubular section 52 is fixed to a proximal portion of the tubular member body section 51 so as to envelop or surround the small-diameter section 51a of the tubular member body section 51. Therefore, the small-diameter section 51a of the tubular member body section 51 constitutes an annular projected section projecting toward the inner side and the proximal side of the tubular member 5. The space between the annular projected section and an inner surface of the stent-containing tubular member 5 (specifically, a distal portion of the tubular section 52) forms an annular gap section. In addition, in this embodiment, the distal portions 69 (69a, 69b) of the wires 6 (6a, 6b) are fixed at an outer surface of the small-diameter section 51a. The gap section is filled with the fixing agent (adhesive), by which the tubular member body section 51 and the tubular section 52 are united together. In addition, by the fixing agent or the like filling the annular gap section, the distal portions (fixing points) 69 (69a, 69b) of the wires 6 (6a, 6b) described later are fixed to the tubular member 5. An adhesive such as an epoxy resin, a UV-curing resin, a cyanoacrylate resin, etc. is preferably used as the fixing agent; however, heat fusing (welding) may also be adopted.

In the stent-containing tubular member 5 used in this embodiment, the tubular member body section 51 exclusive of the small-diameter section 51a and the tubular section 52 are approximately equal in outside diameter. The outside diameter of a stent-containing part of the tubular member body section 51 is preferably about 1.0 to 4.0 mm, particularly 1.5 to 3.0 mm. In addition, the length of the stent-containing tubular member 5 is preferably about 20 to 400 mm, particularly 30 to 300 mm. Besides, the length of the tubular member body section 51 is preferably about 10 to 200 mm, particularly 15 to 150 mm, and the length of the tubular section 52 is preferably about 10 to 200 mm, particularly 15 to 150 mm.

The stent-containing tubular member 5 is not restricted to the one composed of the tubular member body section 51 and the proximal-side tubular section 52 as above-mentioned, but may be an integral one.

The slide tube 7 is so disposed that its distal end is close to the proximal end of the stent-containing tubular member 5. In addition, the slide tube 7 is one which can be contained into the fixed tube, starting from the proximal side thereof. The slide tube 7 may be one which can be fitted over the fixed tube 8, starting from the proximal side thereof. The slide tube 7 can be moved toward the proximal direction together with the stent-containing tubular member 5 by pulling the wires 6 and which is not fixed to the stent-containing tubular member 5.

In the stent delivery system 1 shown in FIGS. 2 to 8, the slide tube 7 includes the slide tube body 71, and the distal-side tubular member 72 which is fixed to a distal portion of the slide tube body 71, which covers the distal end of the slide tube body 71 and which extends distally beyond the distal-most end of the slide tube body 71 toward the distal side of the stent delivery system 1. The distal-side tubular member 72 is an integrally molded tubular body having an intermediately located reduced-diameter section 73 between the distal end and the proximal end of the distal-side tubular member 72 and which is reduced at least in inside diameter. In addition, in this embodiment, the inside diameter of the reduced-diameter section 73 is approximately equal to, or slightly greater than or slightly smaller than the inside diameter of the slide tube body 71. Further, in the stent delivery system 1 in this embodiment, as shown in FIGS. 2 to 8, the distal-side tubular member 72 is one in which the outside diameter and the inside diameter of at least its section other than the reduced-diameter section 73 are greater than those of the slide tube body 71. In addition, the reduced-diameter section 73 is located between the distal end and the proximal end of the distal-side tubular member 72, specifically, a little on the proximal side relative to the distal end of the distal-side tubular member 72. That is, the distance between the distal-most end of the reduced-diameter section 73 and the distal-most end of the distal-side tubular member 72 is less than the distance between the proximal-most end of the reduced-diameter section 73 and the proximal-most end of the distal-side tubular member 72.

In the stent delivery system 1 in this embodiment, a ring-shaped member 75 is located between the distal end of the slide tube body 71 and the reduced-diameter section 73 of the distal-side tubular member 72. In addition, the wires 6a and 6b are fixed to the ring-shaped member 75. The inside diameter of the reduced-diameter section 73 of the distal-side tubular member 72 is greater than the outside diameter of the distal-side tube 2. Therefore, the distal-side tubular member 72 can be moved toward the proximal side, without making contact with the distal-side tube 2. In addition, the inside diameter of the reduced-diameter section 73 of the distal-side tubular member 72 is smaller than the outside diameter of the ring-shaped member 75. Therefore, it restricts movement of the ring-shaped member 75 in the distal direction. With the wires 6a and 6b pulled toward the proximal side, the slide tube 7 is moved toward the proximal side together with the ring-shaped member 75. In addition, the ring-shaped member 75 is fixed to neither of the slide tube body 71 and the distal-side tubular member 72, and is turnably (rotatably) contained between the distal end of the slide tube body 71 and the reduced-diameter section 73 of the distal-side tubular member 72. The distal-side tubular member 72 of the slide tube 7 permits turning of the ring-shaped member 75, and large movement of the ring-shaped member 75 in the axial direction is substantially inhibited by the reduced-diameter section 73 and the distal end of the slide tube body 71. Thus, the ring-shaped member 75 is turnable or rotatable relative to the slide tube 7, whereby it is ensured that the ring-shaped member 75, the fixing part for the wires and the wires themselves cannot easily follow up the turning of the distal-side tubular member 72 (the slide tube 7). That is, the member 75 and the wires do not rotate together with the member 72. A resin ring 76 may be disposed between the ring-shaped member 75 and the distal end of the slide tube body 71. Arrangement of such a resin ring helps ensure that the ring-shaped member 75 can be turned more easily. The resin ring is preferably one which shows relatively little frictional resistance. As the resin ring, there can be preferably used fluoro polymers such as ETFE, etc., PEEK (polyether-ether ketone), polyimides, etc.

Figure 7:
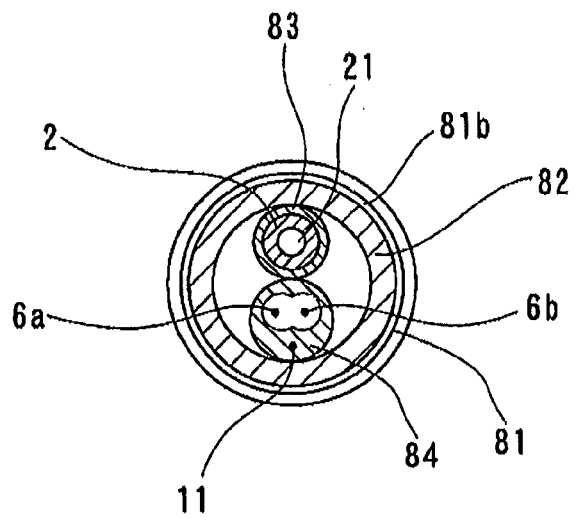
FIG. 7 is an enlarged cross-sectional view taken along the section line VII-VII of FIG. 2.
Figure 8:
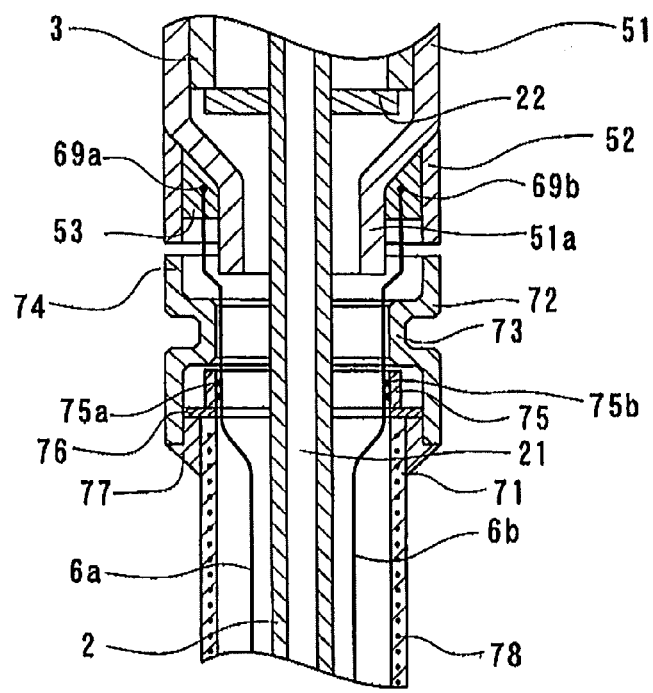
FIG. 8 is an enlarged cross-sectional view of a proximal portion of a stent-containing tubular member and a distal portion of a slide tube, in the stent delivery system of FIG. 1.

As shown in FIGS. 2 to 8, the slide tube 7 specifically includes the slide tube body 71, and the distal-side tubular member 72 which is fixed to the distal portion of the slide tube body 71 and which is greater than the slide tube body 71 in outside diameter and inside diameter. In addition, in this embodiment, as shown in FIG. 8, the distal-side member 72 of the slide tube 7 includes a distal portion 74 and a proximal portion, and the reduced-diameter section 73 provided between the distal portion and the proximal portion (specifically, at a position a little on the proximal side of the distal portion 74). In this embodiment, the reduced-diameter section 73 is reduced in both outside diameter and inside diameter. The reduced-diameter section 73 may be one which is reduced in only inside diameter. The inside diameter of the reduced-diameter section 73 is somewhat greater than the outside diameter of the distal-side tube 2 and is smaller than the outside diameter of the ring-shaped member 75, as above-mentioned. In addition, the reduced-diameter section 73 extends in the axial direction while having substantially the uniform inside diameter over a predetermined length. This reduces the deformation of the distal-side tubular member 72, and permits excellent movement, at the time of pulling the wires (in other words, at the time of movement of the distal-side tubular member 72 in the proximal direction). A proximal portion of the distal-side tubular member 72 is fixed to a distal portion of the slide tube body 71 by an adhesive 77. In addition, the resin ring 76 may be disposed between the ring-shaped member 75 and the distal end of the slide tube body 71 so as to prevent inflow of the adhesive 77 into the ring-shaped member 75.

A distal portion of the slide tube body 71 enters into or is positioned in a proximal portion of the distal-side tubular member 72, and is spaced proximally by a predetermined distance from the reduced-diameter section 73. As a result, an annular recess portion constituting a ring-shaped member holding section is formed between the distal portion of the slide tube body 71 and the reduced-diameter section 73 of the distal-side tubular member 72. In addition, the ring-shaped member 75 is contained in the annular recess portion serving as the ring-shaped member holding section. The ring-shaped member 75 is fixed to neither of the slide tube body 71 and the distal-side tubular member 72 and, therefore, it can be turned or rotated. However, its movement in the axial direction in the slide tube 7 is impossible, except for the clearance between the distal portion of the slide tube body 71 and the reduced-diameter section 73 of the distal-side tubular member 72. The ring-shaped member 75 is preferably a metallic ring.

As shown in FIG. 8, the wires 6a and 6b are fixed to an inner surface of the ring-shaped member 75 by fixing sections 75a and 75b. Fixation of the wires 6a and 6b is preferably carried out by welding, an adhesive, or the like. In addition, since the wires 6a and 6b are fixed to the ring-shaped member 75, pulling of the wires 6a and 6b leads to pulling of the ring-shaped member 75 as well, and the slide tube 7 is also moved toward the proximal end of the stent delivery system 1 by being pushed from the distal side by the ring-shaped member 75.

The distal-side tubular member 72 of the slide tube 7 preferably has its distal portion 74 enveloping or surrounding (i.e., axially overlapping) a proximal portion of the small-diameter section 51a of the stent-containing tubular member 5. In addition, the distal-side tubular member 72 of the slide tube 7 and the stent-containing tubular member 5 are preferably not joined to each other. In this embodiment, as shown in FIGS. 4 and 8, the distal portion of the distal-side tubular member 72 of the slide tube 7 envelops the proximal portion of the small-diameter section 51a of the stent-containing tubular member 5, both being not joined to each other and, further, not being in contact, or substantially in contact, with each other.

Furthermore, in this embodiment, the entire slide tube body 71 is provided with a reinforcement layer 78. Provision of such a reinforcement layer enhances anti-kinking property and helps ensures favorable sliding of the slide tube 7. The reinforcement layer is preferably a meshed reinforcement layer. The meshed reinforcement layer is preferably formed by use of braid wires. The braid is, for example, wire braid, which can be formed by use of metallic wires of stainless steel, elastic metal, superelastic alloy, shape memory alloy or the like, having a wire diameter of 0.01 to 0.2 mm, preferably 0.03 to 0.1 mm. Alternately, the braid may be formed by use of synthetic fiber such as polyamide fiber, polyester fiber, polypropylene fiber, etc.

In the stent delivery system 1 in this embodiment, as shown in FIGS. 2 to 4, 7 and 9, the fixed tube 8 includes a distal-side fixed tube 81 having a large outside diameter, and a proximal-side fixed tube 82 fixed to a proximal portion of the distal-side fixed tube 81. In addition, the distal-side fixed tube 81 has a distal reduced-diameter section 81a, and an inner surface of the distal reduced-diameter section 81a is in contact with an outer surface of a proximal portion of the slide tube 7. The slide tube 7 is not fixed to the distal-side fixed tube 81, and, by sliding in the proximal direction, the slide tube 7 enters into and is contained in the distal-side fixed tube 81.

While the slide tube 7 is preferably contained into the fixed tube 8 through sliding as in this embodiment, this configuration is not limitative; a configuration may be adopted in which sliding of the slide tube toward the proximal side results in the slide tube being fitted over the fixed tube.

Figure 9:
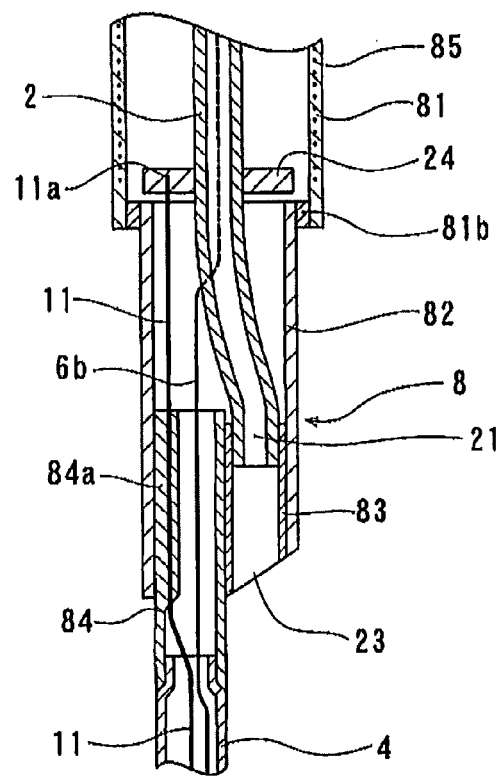
FIG. 9 is an enlarged cross-sectional view of a proximal side portion of a fixed tube in the stent delivery system of FIG. 1.

A distal portion of the proximal-side fixed tube 82 enters into the proximal end of the distal-side fixed tube 81, and is fixed by a fixing section 81b. In addition, a slide tube lock section 24 is provided on and fixed to the outer surface of the distal-side tube 2 in the fixed tube 8, specifically, as shown in FIG. 9, on the outer surface of the distal-side tube 2 at a position corresponding to a proximal portion of the distal-side fixed tube 81. The slide tube 7 can slide toward the proximal direction until it comes into abutment on the slide tube lock section 24. In other words, by abutment of the slide tube 7 on the slide tube lock section 24, further movement of the slide tube 7 in the proximal direction is restricted.

Further, in this embodiment, as shown in FIG. 9, a distal-side portion of the fixed tube 8, specifically, the distal-side fixed tube 81, is provided with a reinforcement layer 85 over substantially the entire length of the distal-side fixed tube 81. Preferable examples of the reinforcement layer include meshed ones, spiral ones, and the like. Particularly, a meshed reinforcement layer is preferred. The meshed reinforcement layer is preferably one which is formed in a meshed form from a thin metallic wire. As the thin metallic wire, stainless steel is preferred. Furthermore, as shown in FIG. 9, the reinforcement layer is preferably absent at a part constituting a connection portion for connection to the proximal-side fixed tube 82.

At a proximal portion of the distal-side tube 2, a tubular firm attachment member 83 is provided. This tubular firm attachment member 83 contains therein the proximal portion of the distal-side tube 2. In addition, at the distal end of the proximal tube 4, the tubular fixation member 84 is provided.

As shown in FIGS. 7 and 9, the tubular firm attachment member 83 and the tubular fixation member 84 axially overlap one another and are firmly attached to the proximal-side fixed tube 82.

As shown in FIGS. 2 and 3, the stent delivery system 1 includes a plurality of (specifically, two) the wires 6a and 6b. Of the wires 6a and 6b, portions of the fixing points 69a and 69b are fixed to the outside of the small-diameter portion of the stent-containing tubular member 5 by the fixing agent 53, in the gap section possessed by the tubular member 5 mentioned above. The wires 6a, 6b and the fixing points 69a, 69b are spaced from each other by a predetermined distance.

Preferable examples of materials for forming the stent-containing tubular member 5 (the tubular member body section 51, the tubular section 52), the slide tube 7 (the slide tube body 71, the distal-side tubular member 72), and the fixed tube 8 (the distal-side fixed tube 81, the proximal-side fixed tube 82), in consideration of the physical properties (flexibility, hardness, strength, sliding properties, anti-kinking property, retractility) required of these members and tubes, include polyethylene, polypropylene, nylons, polyethylene terephthalate, polyimides, fluoro polymers such as PTFE, ETFE, etc. and, further, thermoplastic elastomers. Thermoplastic elastomers are appropriately selected from among those based on nylon (for example, polyamide elastomer), those based on urethane (for example, polyurethane elastomer), those based on polyester (for example, polyethylene terephthalate elastomer), and those based on olefin (for example, polyethylene elastomer, polypropylene elastomer).

Furthermore, an outer surface of the stent-containing tubular member 5 is preferably subjected to a treatment for showing lubricity. Examples of such a treatment include a method in which a hydrophilic polymer such as polyhydroxyethyl methacrylate, polyhydroxyethyl acrylate, hydroxypropyl cellulose, methyl vinyl ether-maleic anhydride copolymer, polyethylene glycol, polyacrylamide, polyvinyl pyrrolidone, etc. is coated to or fixed on the outer surface. In addition, the above-mentioned hydrophilic polymer may be coated to or fixed on an inner surface of the stent-containing tubular member 5, in order to improve sliding properties of the stent 3 therein.

The stent-containing tubular member 5 may be formed from a combination of a two-layer structure of the above-mentioned polymers (for example, nylon for the outer surface, and PTFE for the inner surface).

The stent delivery system 1 has the wires 6 of which one-side end portions are fixed to a proximal portion of the stent-containing tubular member 5 and which extend beyond the proximal end of the stent-containing tubular member 5, penetrate the slide tube 7 and the fixed tube 8, and extend inside the proximal-side tube 4. In addition, with the wire 6 pulled toward the proximal end (i.e., in the proximal direction) of the proximal-side tube, the stent-containing tubular member 5 and the slide tube 7 are moved toward the proximal side (in the proximal direction).

As shown in FIGS. 1, 2, 5 to 8 and 10, the wires 6a, 6b are fixed to a proximal portion of the stent-containing tubular member 5 by the fixing points 69a, 69b provided at a part considerably close to the stent. In addition, the wires 6a, 6b and the fixing points 69a, 69b are so disposed as to be spaced from each other by a predetermined distance.

Further, in this embodiment, the wires 6a and 6b are fixed to a member which is moved by pulling. Specifically, as shown in FIG. 8 and as above-mentioned, the wires 6a and 6b are fixed also to the ring-shaped member 75 (more specifically, its inner surface) possessed by the slide tube 7. Therefore, in the stent delivery system 1 in this embodiment, with the wires 6a and 6b pulled toward the proximal side (i.e., in the proximal direction), the ring-shaped member 75 is also pulled toward the proximal side, and, due to the abutment of the slide tube 7 (the slide tube body 71) on the ring-shaped member 75, the slide tube is also pulled toward the proximal side (i.e., in the proximal direction). Therefore, in this embodiment, the stent-containing tubular member 5 and the slide tube 7 are individually pulled separately, and the stent-containing tubular member 5 and the slide tube 7 do not make contact with each other at the time of pulling. Forces at the time of pulling of the wires 6a, 6b are dispersed to the fixing points 69a, 69b and the fixing sections 75a, 75b of the ring-shaped member 75, which is a member moved by pulling, so that the fixation between the wires 6a, 6b and the stent-containing tubular member 5 at the fixing points 69a, 69b is securely prevented from being canceled.

In the stent delivery system 1 in this embodiment, as shown in FIG. 1, the wires 6 penetrate the proximal-side tube 4 and extend beyond the proximal-most end of the proximal-side tube 4.

As the material constituting the wire, a wire or a material obtained by stranding a plurality of wires can be preferably used. In addition, the wire diameter of the wires is not particularly limited, and, normally, it is preferably about 0.01 to 0.55 mm, more particularly about 0.1 to 0.3 mm.

Examples of the material for forming the wires 6 include stainless steel wires (preferably, spring high-tension stainless steel), piano wires (preferably, piano wires plated with nickel or chromium), superelastic alloy wires, wires formed from various metals such as Ni—Ti alloy, Cu—Zn alloy, Ni—Al alloy, tungsten, tungsten alloy, titanium, titanium alloy, cobalt alloy, tantalum, etc., polymer materials of comparatively high rigidity such as polyamides, polyimides, superhigh-molecular weight polyethylene, polypropylene, fluororesin, etc. and appropriate combinations of these materials.

In addition, side surfaces of the wires may be coated with a low-frictional resin for increasing lubricity. Examples of the low-frictional resin include fluororesins, 6,6-nylon, polyether-ether ketone, and high-density polyethylene. Among these, more preferred are fluororesins. Examples of the fluororesins include polytctrafluoroethylene, polyvinylidene fluoride, ethylene tetrafluoroethylene, and perfluoroalkoxy resins. Further, coatings of silicone or various hydrophilic resins may also be adopted.

Furthermore, in the stent delivery system 1 in this embodiment, a rigidity-imparting body 11 is provided, separately from the above-mentioned wires. As shown in FIGS. 1 to 4, 7 and 9, the rigidity-imparting body 11 extends from the proximal side of the stent delivery system 1, passes inside the proximal-side tube 4 and, further, enters into the fixed tube 8. The distal end 11a of the rigidity-imparting body 11 is fixed to the slide tube lock section 24, as shown in FIG. 9. The distal end 11a of the rigidity-imparting body 11 is preferably fixed by embedding it in the material forming the slide tube lock section 24. As shown in FIG. 3, the illustrated version of the wires 6a, 6b are not fixed to the slide tube lock section 24, but pass through passages 24a, 24b formed in the slide tube lock section 24.

Further, in the stent delivery system 1 in this embodiment, as shown in FIG. 9, the rigidity-imparting body 11 is fixed to the tubular fixation member 84 fixed to the fixed tube 8. As shown in FIG. 9, the tubular fixation member 84 is provided with a rigidity-imparting body fixing section 84a extending over a predetermined length in the axial direction. With a distal portion of the rigidity-imparting body 11 thus fixed at two locations, a strong reinforcing effect of the distal portion of the rigidity-imparting body 11 is exhibited. Particularly, this portion reinforces the slide tube lock section 24 when the slide tube 7 abuts on the slide tube lock section 24.

In addition, the rigidity-imparting body 11 is preferably fixed, at its proximal portion, to a proximal portion of the proximal-side tube 4 or to the operating section 10 which will be described later. Provision of such a rigidity-imparting body 11 makes it possible to restrain deformation of the stent delivery system at the time of pulling of the wires 6. The distal end 11a of the rigidity-imparting body 11 may be formed to be a flat section, for securing fixation by the slide tube lock section 24. Further, it may be provided with means for preventing its disengagement from the fixing member, by forming a wavy part in the side surface thereof.

As the rigidity-imparting body 11, a wire or a material obtained by stranding a plurality of wires may be preferably used. In addition, the diametral size (thickness) of the rigidity-imparting body 11 is not particularly limited, and, normally, it is preferably about 0.01 to 1.5 mm, more preferably about 0.1 to 1.0 mm.

The rigidity-imparting body 11 is preferably one in which its body-side portion (specifically, its portion to be located inside the proximal-side tube) is relatively high in rigidity (for example, large in wire diameter) and its distal-side portion is relatively low in rigidity (for example, small in wire diameter). Further, its section at a change point between both these portions is a tapered section where the wire diameter varies in a tapered manner.

In addition, examples of the material for forming the rigidity-imparting body 11 include stainless steel wires (preferably, spring high-tension stainless steel), piano wires (preferably, piano wires plated with nickel or chromium), superelastic alloy wires, wires formed from various metals such as Ni—Ti alloy, Cu—Zn alloy, Ni—Al alloy, tungsten, tungsten alloy, titanium, titanium alloy, cobalt alloy, tantalum, etc. The rigidity-imparting body 11 is preferably harder than the wires 6.

Figure 11:
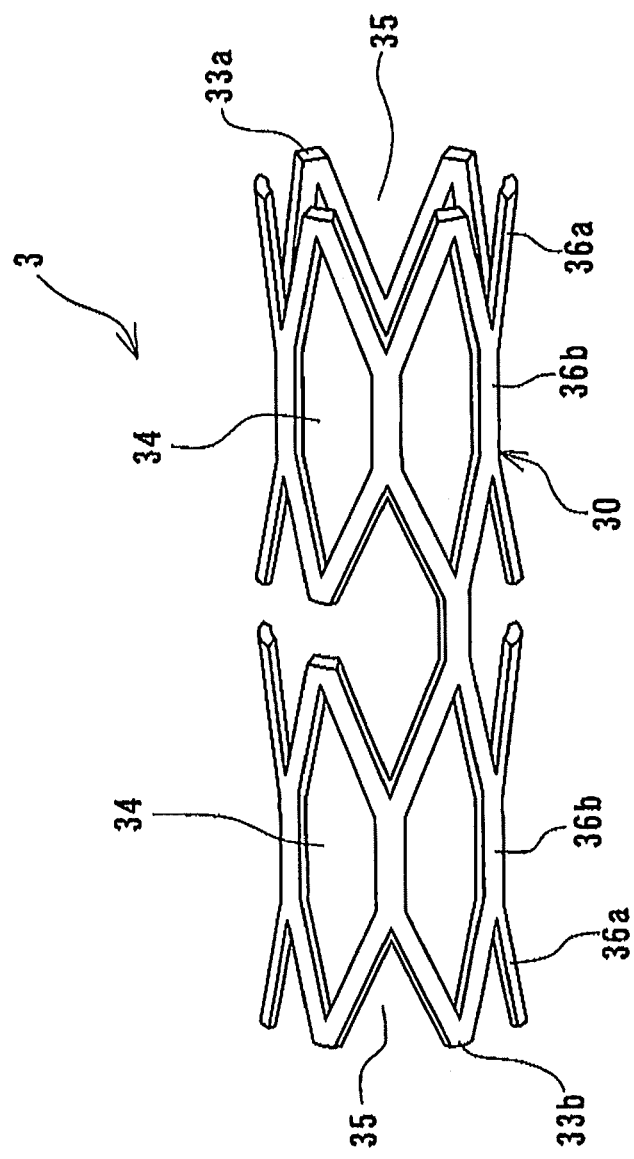
FIG. 11 shows an external appearance of an example of a stent used in the stent delivery system disclosed here.

In the stent-containing tubular member 5 is contained the stent 3. The stent 3 may be any stent that is of the so-called self-expandable type. For example, as the stent 3, one which has a shape as shown in FIG. 11 (a state having been expanded to restore its pre-compression shape is shown) can be used preferably. The stent 3 in this example has a cylindrical frame body 30, openings 34 defined (surrounded) by frames 36a and 36b constituting the cylindrical frame body 30, and cutouts 35 defined by the frames 36a, and the frame body 30 has both end portions 33a, 33b.

The stent is produced, for example, by a method in which a superelastic alloy-made pipe (described later) having an outside diameter adapted to an in-vivo part where the stent is to be put indwelling is prepared, and a side surface of the pipe is partly removed by cutting (for example, mechanical cutting, laser beam cutting), chemical etching or the like to thereby form a plurality of cutouts or a plurality of openings in the side surface.

Since the stent 3 has the cutouts 35 at end portions of the frame body 30, deformation of the end portions 33a and 33b occurs relatively easily; particularly, partial deformation of the end portions is possible, so that the stent 3 shows excellent response to deformation of a blood vessel where the stent 3 is put indwelling. In addition, since the end portions 33a and 33b are composed of end portions of the plurality of frames 36a, they are not so susceptible to collapsing and have sufficient strength. The openings 34 are formed between both end portions of the stent. The openings 34 are surrounded by the frames 36a and 36b, and the openings 34 are relatively easily deformed through deformation of the frames 36a. Therefore, deformation of a central portion of the stent 3 (a central portion of the frame body 30) also occurs relatively easily. The cutouts and the openings are not restricted to the shapes and numbers shown in the figure; the number of the cutouts is preferably about 3 to 10, and the number of the openings is about 3 to 10.

The frame body 30 has an outside diameter of 2.0 to 30 mm, preferably 2.5 to 20 mm, an inside diameter of 1.4 to 29 mm, preferably 1.6 to 28 mm, and a length of 10 to 150 mm, preferably 15 to 100 mm.

The shape of the stent is not limited to the one shown in FIG. 11. Examples of the applicable stent shape include a shape in which trapezoidal cutouts are formed in both end portions and a plurality of hexagonal openings are formed in a honeycomb manner in a central portion, and a shape in which a rectangular cutouts are formed in both end portions and a plurality of rectangular openings (having a length of two times the length of the cutout) are formed in a central portion. Further, the shape of the stent 3 is not restricted to the above-mentioned shapes insofar as it permits the stent to be reduced in diameter at the time of insertion thereof and to be enlarged in diameter (restored) upon discharge (release) into a living body. Examples of the applicable stent shape include a coil-like shape, a cylindrical shape, a roll-like shape, an irregularly shaped pipe-like shape, a high-order coil-like shape, a board spring coil-like shape, and a cage- or mesh-like shape.

Superelastic alloys are preferably used as the material forming the stent. The superelastic alloys here are alloys which are generally called shape memory alloys and show superelasticity at least at a body temperature (around 37° C.). Particularly, such superelastic metals as Ti—Ni alloys containing 49 to 53 atomic % of Ni, Cu—Zn alloys containing 38.5 to 41.5 wt % of Zn, Cu—Zn—X alloys (X=Be, Si, Sn, Al, Ga) containing 1 to 10 wt % of X, and Ni—Al alloys containing 36 to 38 atomic % of Al are preferably used. Especially preferred are the above-mentioned Ti—Ni alloys. Besides, mechanical properties of the alloys can be appropriately changed by conversion of the Ti—Ni alloys into Ti—Ni—X alloys (X=Co, Fe, Mn, Cr, V, Al, Nb, W, B or the like) through replacing part of the Ti—Ni alloys with 0.01 to 10.0% of X, by conversion of the Ti—Ni alloys into Ti—Ni—X alloys (X=Cu, Pb, Zr) through replacing part of the Ti—Ni alloys with 0.01 to 30.0% of the relevant atoms, or by selection of a cold work ratio or/and final heat treatment conditions. In addition, mechanical properties of alloys can be appropriately changed by using the above-mentioned Ti—Ni—X alloys and selecting a cold work ratio and/or final heat treatment conditions.

The superelastic alloy to be used has a buckling strength (yield stress under load) of 5 to 200 kgf/mm$^2$ (22° C.), preferably 8 to 150 kgf/mm$^2$, and a restoring stress (yield stress when unloaded) of 3 to 180 kgf/mm$^2$ (22° C.), preferably 5 to 130 kgf/mm$^2$. The superelasticity here means such a property that, even after deformation (bending, tension, compression) of a material into a region where ordinary metals are plastically deformed at a use temperature, the shape of the material before compression is substantially restored upon release of the deformation, without need for heating.

The stent used in the stent delivery system disclosed here may be one which includes a stent body formed in a cylindrical shape (inclusive of substantially cylindrical shape) and capable of being reduced in diameter, and a tubular cover (not shown) for sealing a side surface of the stent body.

The stent delivery system described here is not restricted to the above-described embodiment. Particularly, the stent delivery system in the embodiment above is of the so-called rapid exchange type in which a guide wire insertion port is provided at a side portion on the distal side. But the system is not limited in that regard. The stent delivery system may also be of the so-called over-the-wire type in which a guide wire lumen extends from the distal end to the proximal end of a tube body.

In addition, as shown in FIGS. 1 and 12 to 27, the stent delivery system 1 according to the example described here has the operating section 10 fixed to the proximal end of the proximal-side tube 4.

The operating section 10 in the stent delivery system 1 in this embodiment has, in addition to a wire winding mechanism and a wire winding amount restriction mechanism, a lock mechanism for unlockably locking the rotation of the wire winding mechanism and a reverse rotation restriction mechanism for restricting rotation of the wire winding mechanism in a reverse direction relative to the winding direction of the wires.

The wire winding mechanism has the winding shaft section 63 coaxial and integral with the operating rotary roller 61, and smaller than the operating rotary roller 61 in outer diameter. The winding shaft section 63 holds proximal portions of the wires 6a, 6b. The wire winding amount restriction mechanism is composed of the Geneva gear mechanism which includes the driving gear 12 (Geneva wheel) coaxial and integral with the operating rotary roller 61, and the driven gear 40 (Geneva cross) rotated intermittently by the driving gear 12, and, further, has a stopper function for stopping the rotation of the driving gear 12 after rotation of the driving gear 12 by a predetermined amount. Further, the driving gear 12 and the driven gear 40 have a stopper function for stopping the rotation of the driving gear 12 after rotation of the driving gear 12 by a predetermined amount. In addition, the driving gear 12 (Geneva wheel) and the driven gear 40 (Geneva cross) constitute the Geneva gear mechanism.

The operating section 10 has an operating section housing 50, as shown in FIGS. 12 to 18. The operating section housing 50 is composed of a housing body 50a, a cover member 50b and a cap 50c. The operating section housing 50 has a bent and rounded shape on the proximal side and at a central portion thereof, is relatively easy to grip, and permits relatively easy roller operations when in a gripped state.

Figure 17:
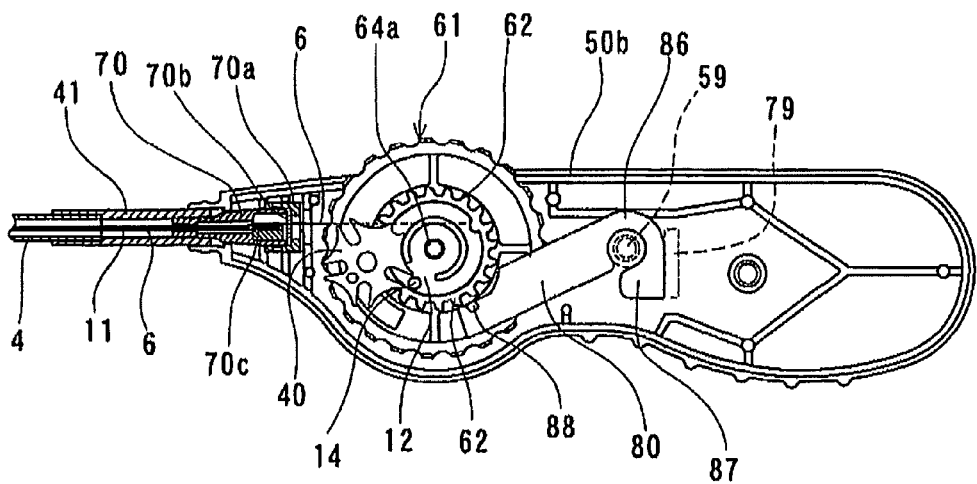
FIG. 17 is an illustration of an internal structure of the operating section of the stent delivery system shown in FIG. 12.

In addition, as shown in FIG. 17, a distal portion of a tubular connector 41 is fixed to the proximal end of the proximal-side tube 4. A seal mechanism connected to a proximal portion of the connector 41 is contained in the operating section housing 50. As shown in FIG. 17, the seal mechanism includes a seal mechanism tubular body member 70 having a distal portion fixed to a proximal portion of the connector 41, a cap member 70a fixed to the proximal end of the tubular body member 70, a seal member 70b disposed between the tubular body member 70 and the cap member 70a, and a rigidity-imparting body fixing member 70c contained in the tubular body member 70. The tubular body member 70 and the cap member 70a are provided with an opening section penetrating therethrough. The seal member 70b is provided with holes or slits which permit the wires 6 (6a, 6b) to pass therethrough in a liquid-tight condition and in a slidable manner. In addition, a proximal portion of the rigidity-imparting body 11 is fixed to the rigidity-imparting body fixing member 70c. The rigidity-imparting body fixing member 70c is fixed in the tubular body member 70.

Figure 12:
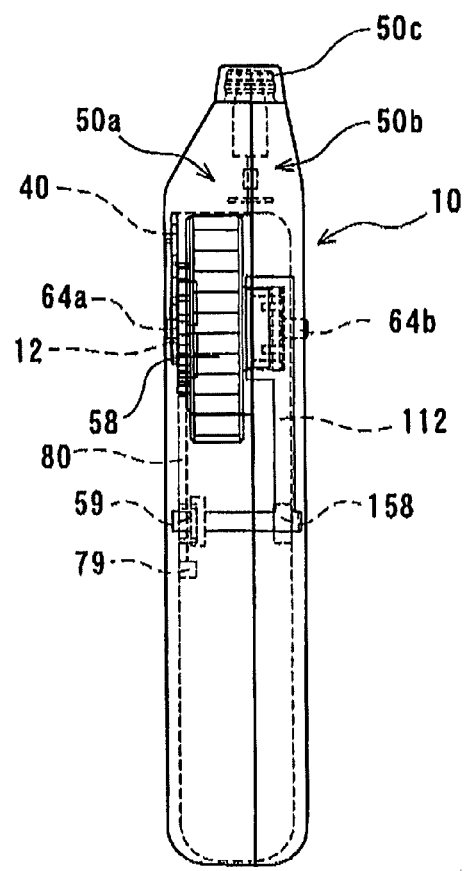
FIG. 12 is an enlarged front view of an operating section of the stent delivery system disclosed here.
Figure 13:
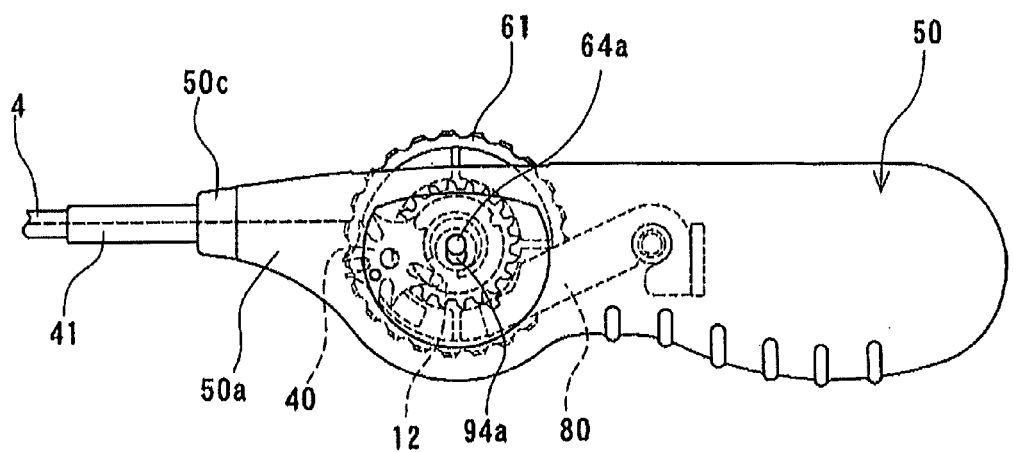
FIG. 13 is a left side view of the vicinity of the operating section of the stent delivery system disclosed here.
Figure 14:
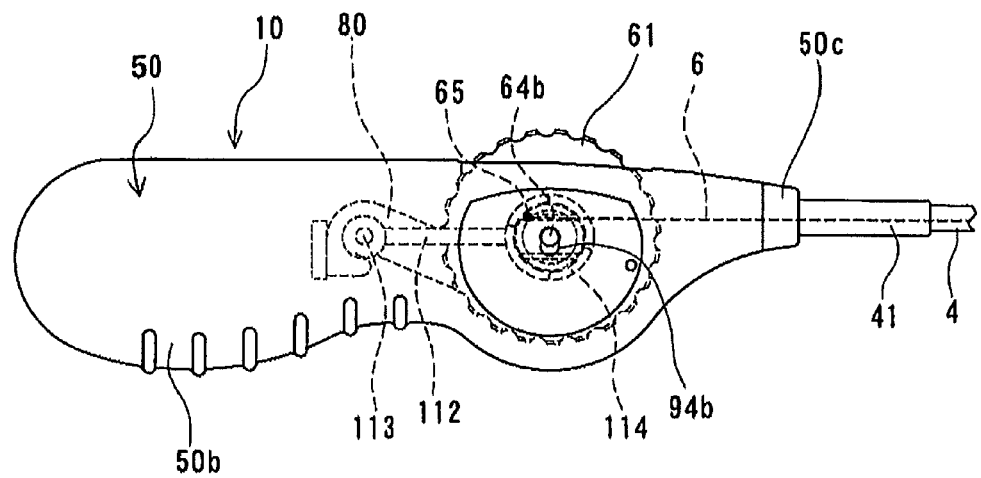
FIG. 14 is a right side view of the vicinity of the operating section of the disclosed stent delivery system.
Figure 15:
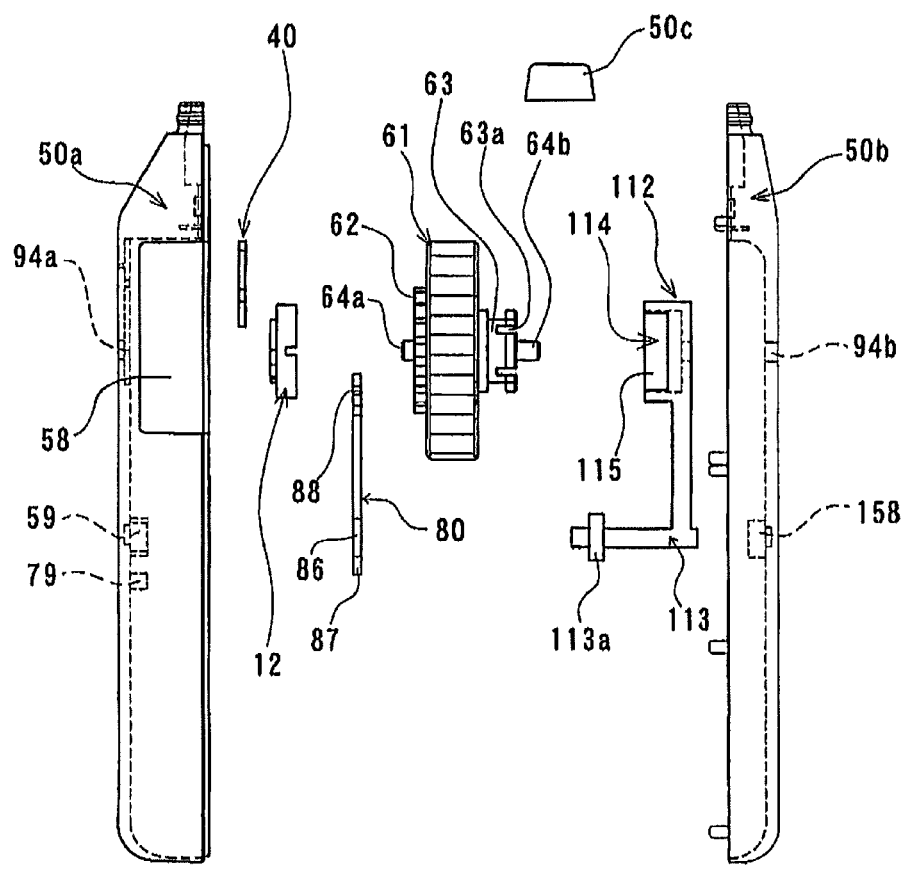
FIG. 15 is an illustration of an internal structure of the operating section of the stent delivery system shown in FIG. 12.
Figure 16:
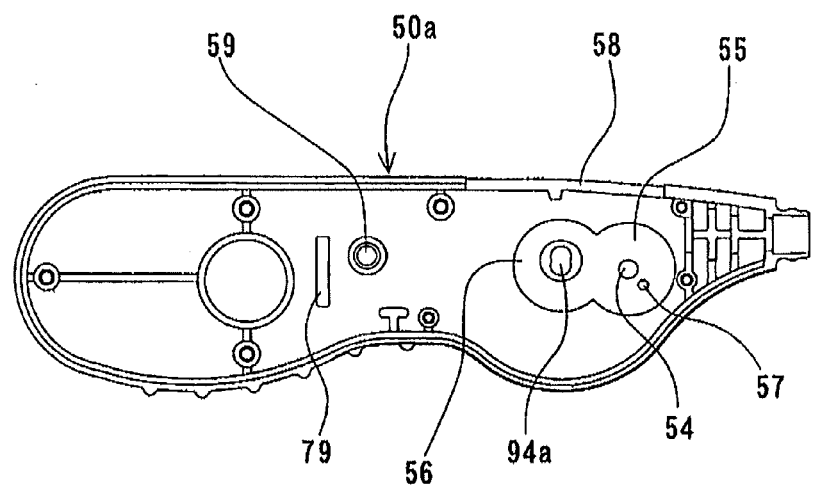
FIG. 16 is an illustration of an internal shape of a housing body of the operating section shown in FIG. 15.
Figure 21:
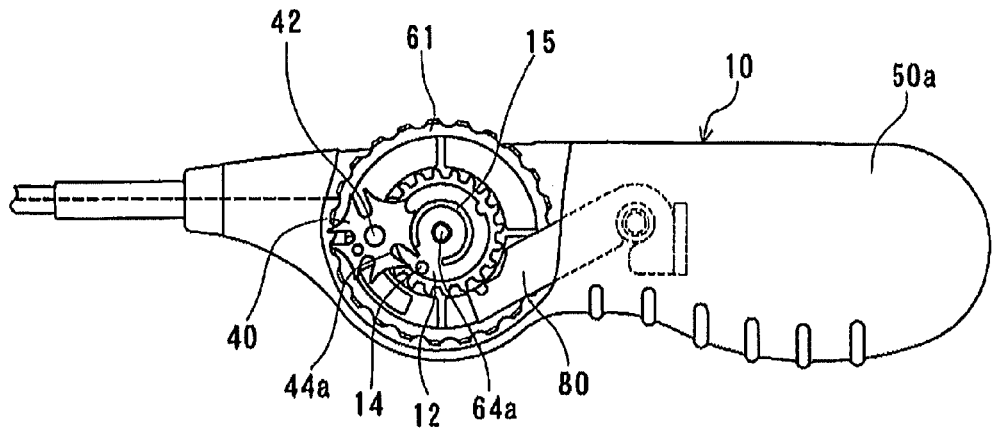
FIG. 21 is an illustration of operation of the operating section of the disclosed stent delivery system

As shown in FIGS. 12 to 18, the housing 50 includes an opening section 58 which receives the operating rotary roller 61 and from which the operating rotary roller 61 partly protrudes, a locking rib for engagement with projected portions of a gear section 62 provided on the roller 61, a bearing section 94b for containing one end 64b of a rotary shaft of the roller 61, and a bearing section 94a for containing the other end 64a of the rotary shaft of the roller 61. The locking rib is so formed as to be able to enter into spaces between the projected portions formed on the gear section 62 of the roller 61. In addition, as shown in FIGS. 13 and 16, the bearing sections 94a, 94b are gourd-shaped so as to contain the one end 64b and the other end 64a of the rotary shaft of the roller 61 and to extend in a direction for spacing away from the above-mentioned opening section. The hearing sections 94a, 94h are not restricted to gourd-shaped bearing sections insofar as they can be moved a distance such as to permit disengagement from the locking rib. For instance, the shape of the bearing sections 94a, 94b may be an oval, rectangular or elliptic shape or the like. Particularly, in the operating section 10 in this embodiment, the above-mentioned bearing sections 94a, 94b are gourd-shaped. By pressing the operating rotary roller 61 so that the end portions 64a, 64b of the rotary shaft of the roller 61 contained in spaces on one end side of the bearing sections 94a, 94b are made to ride over the opposed rib portions formed on the inside surfaces of central portions of the bearing sections 94a, 94b, the end portions 64a, 64b of the rotary shaft of the roller 61 are put into the state of being contained in spaces on the other side of the bearing sections 94a, 94b. The condition shown in FIG. 21 is the condition wherein the roller 61 is pressed. In the pressed state, the roller 61 is pressed by a biasing member. In this case, the end portions 64a, 64b of the rotary shaft of the roller 61 come into contact with the opposed rib portions formed on the inside surfaces of the central portions of the bearing sections 94a, 94b, so that the bearing sections 94a, 94b are not moved into the spaces on the one end side. Consequently, the roller 61 is maintained in the rotatable state.

In addition, in this embodiment, the operating section 10 has a collar member 112, as shown in FIGS. 12, 14 and 15. The collar member 112 has a collar section 114 which contains the winding shaft section 63 therein, and forms an annular space between itself and the winding shaft section 63. The collar section 114 prevents the wires 6 wound up by the winding shaft section 63 from loosening. The collar member 112 also guides the movement of the rotary roller when pressed and suppresses chattering of the rotary roller. A pin 113 of the collar member 112 rotatably bears on a projected section (bearing section) 59 of the housing body 50a and a recess section (bearing section) 158 of the cover member 50b. In addition, the bearing sections 94a, 94b are formed in the shape of a gentle arc of a circle having a center at the pin 113 (bearing sections 59, 158), and has such a length as to permit the roller 61 to be moved a distance of not less than the height of the locking rib. As shown in FIG. 15, the collar member 112 is provided with two opposed cutouts 115 which extend from a side surface and which reach the space inside the collar section 114. The wires 6 pass through the cutout 115 on one side, and are fixed to the winding shaft section 63.

Figure 18:
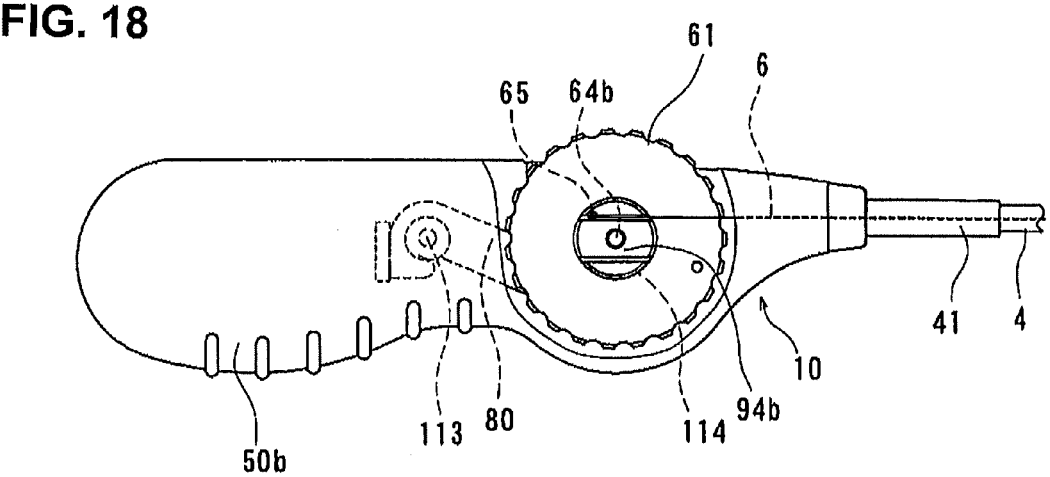
FIG. 18 is an illustration of an internal structure of the operating section of the stent delivery system shown in FIG. 12.

In addition, the wire winding mechanism is composed of the roller 61, and the winding shaft section 63 rotated by rotation of the roller 61. The winding shaft section 63 grips or fixes proximal portions of the wires 6. Specifically, as shown in FIG. 18, the wires 6 are provided at their proximal portions with anchor sections 65 formed to be larger in size than the wires 6, and the winding shaft section 63 is provided with slits 63a capable of containing the wires 6 therein. Proximal portions of the wires 6 are contained in the slits 63a in the winding shaft section 63 so that the anchor sections 65 are located outside the proximal ends of the slits 63a. This helps ensure that when the winding shaft section 63 is rotated, the wires 6 are wound onto an outer surface of the winding shaft section 63. The gripping or fixation of the wires 6 onto the winding shaft section 63 is not restricted to the above-mentioned, and may be of any system. For example, the proximal ends or proximal portions of the wires 6 may be directly fixed to the winding shaft.

In addition, the proximal portions thus wound up of the wires 6 are preferably flexible, so as to permit relatively easy winding. Examples of the method for making the proximal portions of the wires 6 flexible include a method in which the proximal portions of the wires 6 are formed from a flexible material, and a method in which the proximal portions of the wires 6 are relatively small in diameter.

In this embodiment, the winding shaft section 63 is formed integrally with the rotary roller 61 so as to be coaxial with the latter. Further, as shown in FIGS. 12, 15 and 18, the winding shaft section 63 is provided on the side of a side surface on one side of the rotary roller 61. In addition, with the rotary roller 61 rotated, the winding shaft section 63 is also rotated simultaneously. The winding amount of the wires is preferably small, as compared with the rotational operating amount of the rotary roller. This permits slow winding, whereby movement of the stent-containing tubular member toward the proximal side is also relatively slow and favorable. In this embodiment, the outside diameter of the winding shaft section 63 is smaller than that of the rotary operating roller 61, so that the winding amount of the wires is relatively small as compared with the rotational operating amount of the rotary roller.

The outside diameter of the winding shaft section 63 is preferably about 1 to 60 mm, particularly 3 to 30 mm, and the outside diameter of the rotary roller is preferably about 1 to 20 times, particularly 1 to 10 times, the outside diameter of the winding shaft section. The outside diameter of the rotary roller is preferably about 10 to 60 mm, particularly 15 to 50 mm.

The rotary roller and the winding shaft section are not limited to a construction in which they are an integral, one-piece unitary construction. For example, the winding shaft section may be composed of a separate member which is rotated as a result of rotation of the rotary roller. The system of transmitting the rotation of the rotary roller may be of any type, such as gear type or belt type. In addition, a surface part which may be contacted at the time of operating the roller 61 is preferably a difficultly slidable surface. For example, the surface part which may be contacted at the time of operating the roller 61 is preferably subjected to a knurling treatment, an embossing treatment, coating with a high-friction material, or the like.

The stent delivery system 1 in this embodiment has the wire winding amount restriction mechanism, as shown in FIGS. 12, 13, 14 to 17 and 19. The wire winding amount restriction mechanism in this embodiment is composed of the Geneva gear mechanism which includes the driving gear 12 (Geneva wheel) provided coaxially and integrally with the operating rotary roller 61, and the driven gear 40 (Geneva cross) rotated intermittently by the driving gear 12 (and rotatable about an axis non-coaxially arranged relative to the rotation axis of the driving gear). The wire winding amount restriction mechanism in this embodiment also includes a stop performing a stopper function for stopping the rotation of the driving gear 12 after rotation of the driving gear 12 by a predetermined amount.

In this embodiment, the driving gear 12 (Geneva wheel) is mounted to a side surface, on the side opposite to the winding shaft section 63, of the operating rotary roller 61 so as to be coaxial and integral with the latter. In addition, the driving gear 12 is rotated together with the operating rotary roller 61.

Figure 19:
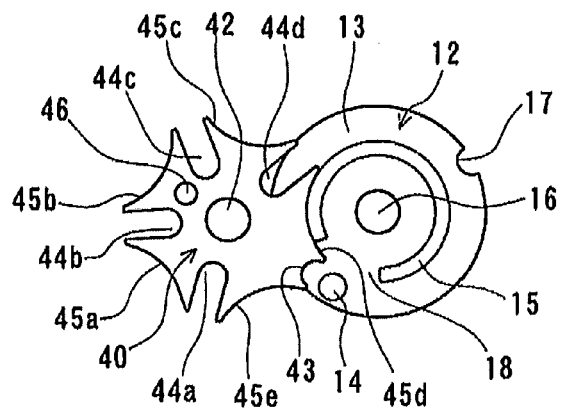
FIG. 19 is an illustration of a Geneva gear mechanism used in the operating section of the stent delivery system disclosed here.

As shown in FIG. 19, the driven gear 40 has a plurality of turning grooves 44a, 44b, 44c, 44d extending by a predetermined length from outer peripheral portions toward a bearing section (rotary shaft) 42, and a single stop portion 43 formed as a stopping recess portion, at substantially equal angular intervals around the rotary shaft 42. In this embodiment, the driven gear 40 has four turning grooves and one stopping recess portion, so that the grooves and recess portion are located at angular intervals of 72° around the rotary shaft. The number of turning grooves is not limited to 4; the number is preferably 3 to 12, particularly 3 to 6. The number of turning grooves is the number of revolutions the roller can be rotated.

The driving gear 12 has a driven gear turning projection 14 which can enter into and be disengaged from the turning grooves 44a, 44b, 44c, 44d of the driven gear 40 and can be engaged with the stopping recess portion 43. In addition, the turning grooves 44a, 44b, 44c, 44d of the driven gear 40 each have a width permitting the driven gear turning projection 14 to enter thereinto and advance therein, and each extend a predetermined length toward the rotary shaft (i.e., radially). The respective turning grooves 44a, 44b, 44c, 44d are all the same in length. The stopping recess portion 43 is a recess portion which does not have a portion extending a predetermined length in the direction of the rotary shaft That is, the stopping recess portion 43 is much more shallow than the turning grooves 44a, 44b, 44c, 44d. In addition, a plurality of outer edge portions between the plurality of turning grooves 44a, 44b, 44c, 44d and the stopping recess portion 43 of the driven gear 40 are commonly shaped arcuate recess portions 45a, 45b, 45c, 45d, 45e, and the driving gear 12 has a circular or arcuate projected section 15 having an outer edge shape corresponding to each of the arcuate recess portions 45a, 45b, 45c, 45d, 45e of the driven gear. The Geneva gear mechanism in this embodiment is of the so-called circumscribed Geneva type. The curvature of each of the arcuate recess portions 45a, 45b, 45c, 45d, 45e is equal to the curvature of the projected section 15. This helps ensure that, even when the driving gear is rotated in the condition where the projected section 15 is in contact with each of the arcuate recess portions 45a, 45b, 45c, 45d, 45e, the frictional resistance therebetween alone will not rotate the driven gear. Further, a section, in the vicinity of the driven gear turning projection 14 (i.e., a section radially aligned with the driven gear turning projection 14 or positioned radially inwardly of the driven gear turning projection 14), of the driving gear 12 is a rib-missing section 18 where the circular or arcuate rib 15 is absent. The rib 15 possesses a circular shape having a radius of curvature, and the rib-missing section 18 possesses the same radius of curvature. The provision of the rib-missing section 18 in the vicinity of the rib 15 helps ensure excellent rotation of the driven gear 40. In addition, the driving gear 12 has a body section 13 for mounting onto the operating rotary roller 61, is provided in its side surface with a recess portion 17 for engagement with the operating rotary roller 61, and is provided in its central portion with an opening 16 which permits the end portion 64a of the rotary shaft of the roller 61 to pass therethrough. The driving gear 12 is smaller in outer diameter than the operating rotary roller.

Further, the operating section housing 50 contains the operating rotary roller 61 with the winding shaft section and the driving gear 12, the driven gear 40, and a proximal portion (connector) 41 of the proximal-side tube 4. Furthermore, as shown in FIG. 16, the operating section housing (specifically, the housing body 50a) has a shaft-forming projection 54 forming a rotary shaft of the driven gear 40, and the driven gear 40 has the bearing section 42 for receiving the shaft-forming projection 54. In this embodiment, the bearing section 42 is an opening formed in a central portion of the driven gear 40. Further, the operating section housing (specifically, the housing body 50a) has a recess portion 55 for containing the driven gear 40, and a recess portion 56 for containing the driven gear turning projection 14 and the rib 15 portion of the driving gear 12, which recess portions are formed in an inner surface of the housing (housing body 50a). In the configuration shown in FIG. 16, the recess portion 55 and the recess portion 56 are connected to each other to form an overall qourd-shaped recess. Further, the driven gear 40 is provided with a driven gear initial state setting through-hole 46, and a driven gear containing section (specifically, the recess portion 55) in the operating section housing (specifically, the housing body 50a) is also provided with a driven gear initial state setting through-hole 57. The driven gear 40 is disposed in the driven gear containing section (specifically, the recess portion 55) so that both the through-holes 46 and 57 match to each other, and thereafter a pin is inserted so as to penetrate both the through-holes, whereby the driven gear 40 can be easily disposed in an initial state. In addition, the driven gear 40 is clamped between an inner surface of the housing body 50a and the operating rotary roller 61, whereby the driven gear 40 is inhibited or prevented from being disengaged from the shaft-forming projection 54.

The operating section 10 in this embodiment has the lock mechanism for unlockably locking the rotation of the wire winding mechanism, and the reverse rotation restriction mechanism for restricting rotation of the wire winding mechanism in the reverse direction relative to the winding direction of the wires.

As shown in FIGS. 12, 13, 15 and 17, the operating rotary roller 61 is provided with a gear section 62 coaxial with and turned integrally as a single unit with the operating rotary roller 61. Further, as shown in FIGS. 15 and 17, the gear section 62 is provided on the side of a side surface on the other side of the rotary roller 61 (in other words, at a surface on the side opposite to a surface where the winding shaft section 63 is provided). Therefore, the gear section 62 and the winding shaft section 63 are partitioned from each other by a wall composed of the operating roller.

In addition, the operating rotary roller 61 is partly exposed from the opening section 58, and this exposed part constitutes an operating section. The rotary roller has the other end 64a of the rotary shaft provided at the side surface on one side (specifically, at a side surface of the gear section 62), and the one end 64b of the rotary shaft provided at the side surface on the other side (specifically, at a side surface of the winding shaft 63).

Further, as shown in FIGS. 13, 15 and 17, a biasing member 80 is provided in the housing 50 for biasing the rotary roller 61 in the direction of the opening section of the housing. Specifically, the roller 61 is biased by the biasing member 80. Furthermore, the housing 50 is provided with the locking rib configured to enter into the spaces between the projected portions of the gear section 62 of the rotary roller 61 biased by the biasing member 80. Therefore, the rotary roller 61, in the state of being biased by the biasing member 80, is not turnable because the locking rib is in engagement with the projected portions of the gear section 62. In addition, when the rotary roller 61 is pushed in the direction for spacing away from the locking rib, the one end 64b and the other end 64a of the rotary shaft of the rotary roller are moved inside the bearing sections 94a and 94b provided in the housing 50, so as to be rotatable. Therefore, the operating section 10 in this embodiment restricts rotation in the condition where the rotary roller 61 is not pressed, and the operating section 10 has the lock mechanism for unlockably locking rotation of the wire winding mechanism.

In the operating section in this embodiment, the above-mentioned biasing member 80 and the above-mentioned gear section 62 constitute the reverse rotation restriction mechanism for restricting rotation of the wire winding mechanism in the reverse direction relative to the winding direction of the wires.

Inside the operating section 10 is provided the reverse rotation restriction mechanism, as shown in FIGS. 13, 15 and 17. In this operating section 10, the biasing member 80 is provided with the reverse rotation restriction mechanism. The reverse rotation restriction mechanism includes an engaging section 88, an elastically deformable section 86, and a mounting section 87 for mounting to the housing. The engaging section 88 is provided at a part, facing the gear section 62 of the operating rotary roller 61, of a distal portion of a reverse rotation restricting member (being also the biasing member) 80 and which can engage with the gear section. In addition, the housing body 50a is provided, at an inner surface thereof, with the first projected section (bearing section) 59 and a second projected section 79. The first projected section 59 enters into the elastically deformable section 86 of the reverse rotation restricting member (biasing member) 80, and has an outer surface shape corresponding to an inner surface shape of the elastically deformable section 86. Specifically, the inner surface shape of the elastically deformable section 86 is an arcuate shape, and the first projected section 59 has a cylindrical outer shape corresponding to the arcuate shape of the inner surface of the elastically deformable section 86. The mounting section 87 of the reverse rotation restricting member (biasing member) 80 has a shape permitting the mounting section 87 to be mounted between the first projected section 59 and the second projected section 79 formed on the housing body 50a. In addition, the reverse rotation restricting member (biasing member) 80 is non-turnably mounted in position, by mounting of its mounting section 87 between the first projected section 59 and the second projected section 79 of the housing body 50a, and biases the operating rotary roller 61 in the direction of the opening section 58, by an elastic force of its elastically deformable section 86. The mounting section 87 of the reverse rotation restricting member (biasing member) 80 is restricted from moving sideways by a circular disk-like projected section 113a provided on the collar member 112.

Figure 20:
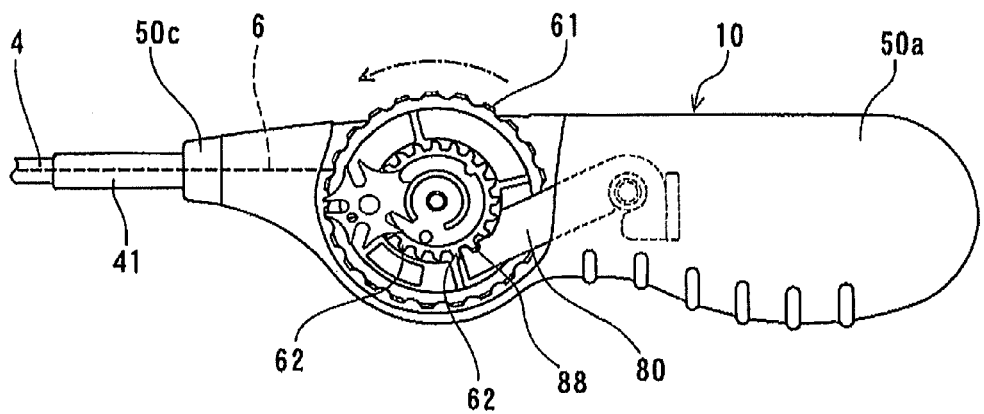
FIG. 20 is an illustration of operation of the operating section of the stent delivery system disclosed here.

As above-mentioned, with the roller 61 pressed, the roller becomes rotatable. However, although rotation in the direction of arrow in FIG. 22 (in the direction for winding the wires 6) is possible, an attempt to rotate the roller 61 in the reverse direction as shown in FIG. 20 causes one tooth portion of the gear section 62 and the engaging section 88 of the reverse rotation restricting member (biasing member) 80 to engage with each other, whereby the attempted rotation is inhibited. By this, rotation of the roller in the reverse direction relative to the direction of winding of the wires 6 by the wire winding mechanism is restricted. In addition, in this operating section 10, as shown in FIG. 12, the reverse rotation restricting member (biasing member) 80 is disposed between an inner surface of the housing body 50a and a side surface of the rotary roller 61. Therefore, movement of the reverse rotation restricting member (biasing member) 80 in a lateral direction (horizontal direction) is restricted by the inner surface of the housing body 50a and the side surface of the rotary roller 61.

The gear section 62 is smaller in outer diameter than the rotary roller 61. The outside diameter of the gear section 62 is preferably about 10 to 60 mm, particularly 15 to 50 mm, and the number of teeth is preferably about 4 to 200, particularly 4 to 70.

The collar member 112 provided in the operating section 10 has one end portion rotatably borne or supported on the pin 113. The collar section 114 on the other end side contains the winding shaft section 63, and forms an annular space between itself and the winding shaft section 63. This annular space is not a considerably large space, and a narrow annular space is formed between outer surfaces of the wound wires.

Now, a method of using the stent delivery system 1 disclosed here will be described below with reference to the drawings.

First, a terminal end of a guide wire is inserted into the opening section 25a of the distal member in the stent delivery system shown in FIGS. 1 and 2, and the guide wire protrudes from the opening 23. Next, the stent delivery system is inserted into a guiding catheter (not shown) having been inserted into a living body, and the stent delivery system 1 is advanced along the guide wire so as to locate the stent-containing part of the stent-containing tubular member 5 in a target stenosed part.

Subsequently, the operating rotary roller 61 of the operating section 10 is depressed, and then the roller is rotated in the direction of the arrow in FIG. 22. This results in the wires 6 being wound onto the outer circumferential surface of the winding shaft 63, and the stent-containing tubular member 5 and the slide tube 7 are moved in the axial direction toward the proximal side. In this instance, a proximal end surface of the stent 3 abuts and is locked on a distal end surface of the stent proximal portion lock section 22 of the distal-side tube 2. Therefore, associated with the movement of the stent-containing tubular member 5, the stent 3 is discharged (released) via the distal opening of the stent-containing tubular member 5. Due to the discharge (release), the stent 3 self-expands as shown in FIG. 10 so as to dilate the stenosed part and so that the stent is indwelling in the stenosed part.

The operation of the wire winding amount restriction mechanism in the stent delivery system 1 disclosed here will be described below with reference to the drawings. FIGS. 21 to 28 are illustrations of operational aspects of the operating section of the stent delivery system disclosed here.

As shown in FIG. 21, with the operating rotary roller 61 of the operating section 10 depressed, the roller 61 becomes rotatable. In an initial state of the operating section 10, as shown in FIGS. 17 and 21, the driven gear 40 has its stopping recess portion 43 disposed to be located at a position most remote from the driving gear 12 (specifically, from the driven gear turning projection 14 of the driving gear), along the rotating direction of the driven gear. Specifically, after the driven gear turning projection 14 of the driving gear passes through all the plurality of turning grooves 44a, 44b, 44c, 44d provided in the driven gear, the driven gear turning projection 14 of the driving gear 12 and the stopping recess portion 43 of the driven gear 40 are engaged with each other. As will be described later, the driven gear 40 is turned only after the entering of the driven gear turning projection 14 of the driving gear into each of the turning grooves 44a, 44b, 44c, 44d until disengagement of the driven gear turning projection 14 from each turning groove. Consequently, the driven gear 40 is turned intermittently by the driving gear 12.

Figure 22:
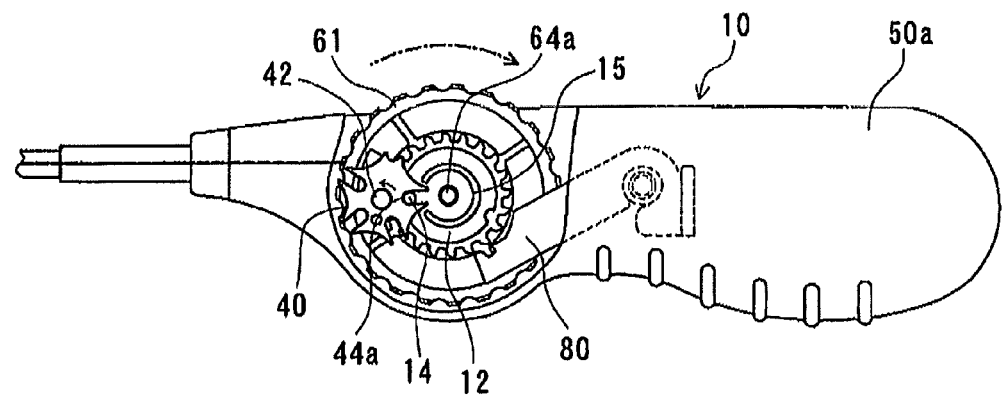
FIG. 22 is an illustration of operation of the operating section of the disclosed stent delivery system.
Figure 23:
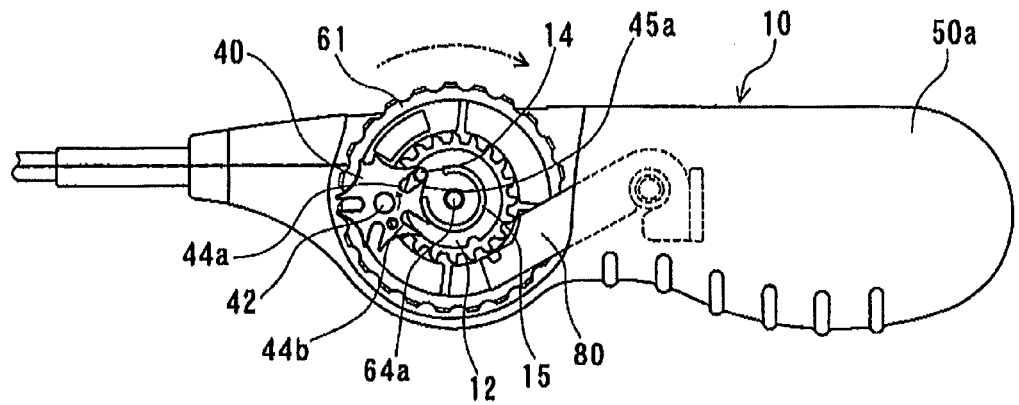
FIG. 23 is an illustration of operation of the operating section of the disclosed stent delivery system.
Figure 24:
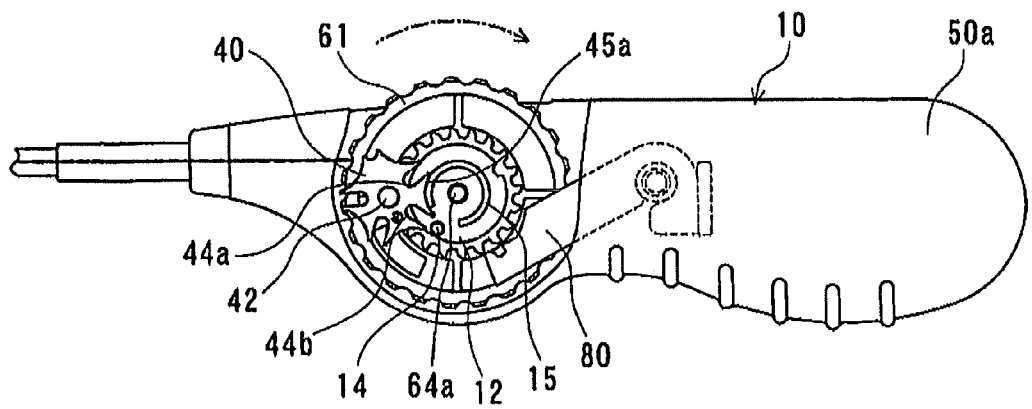
FIG. 24 is an illustration of operation of the operating section of the disclosed stent delivery system.
Figure 25:
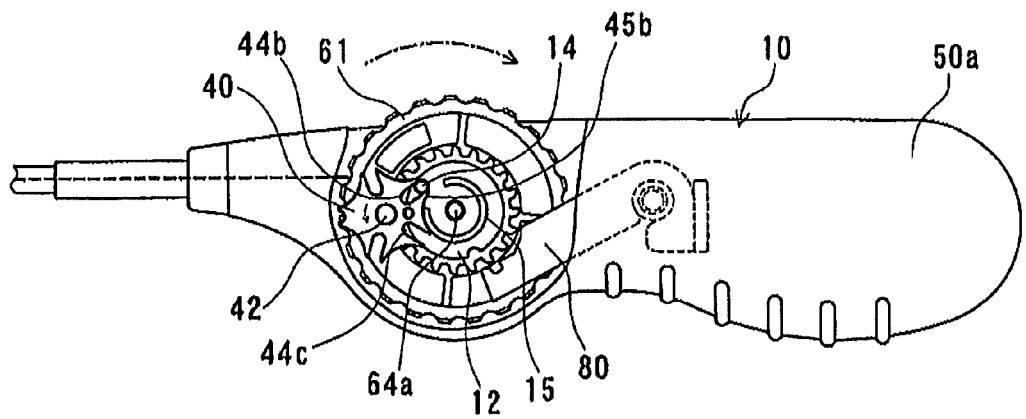
FIG. 25 is an illustration of operation of the operating section of the disclosed stent delivery system.
Figure 26:
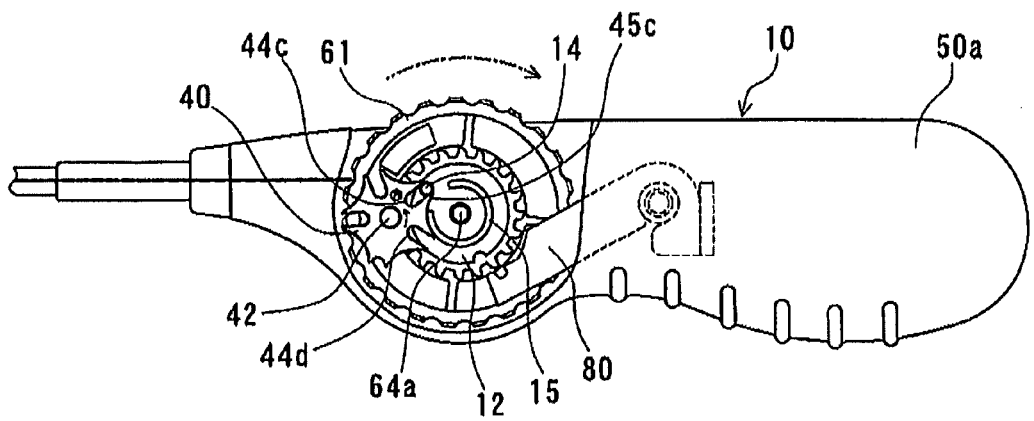
FIG. 26 is an illustration of operation of the operating section of the disclosed stent delivery system.
Figure 27:
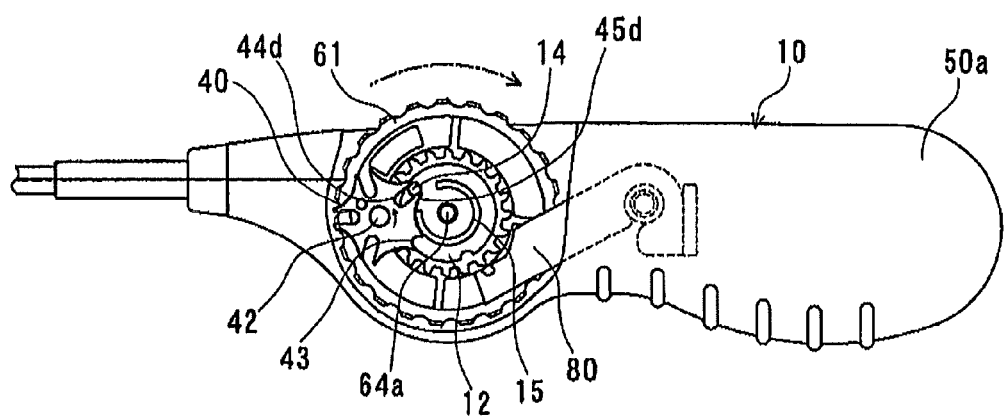
FIG. 27 is an illustration of operation of the operating section of the disclosed stent delivery system.
Figure 28:
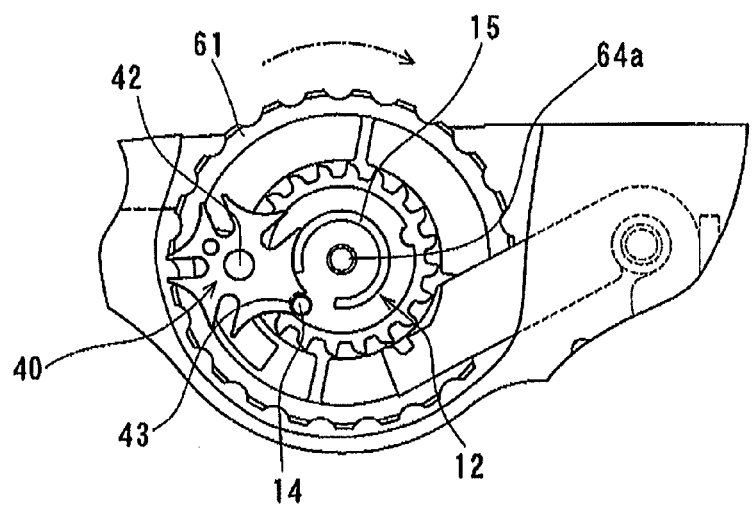
FIG. 28 is an illustration of operation of the operating section of the disclosed stent delivery system.

In addition, with the roller 61 rotated in the direction of the arrow in FIG. 22, the driven gear turning projection 14 of the driving gear 12 enters into the first turning groove 44a of the driven gear 40 and rotates the driven gear 40. FIG. 22 shows the condition where the roller 61 has been rotated by about 55° (the driving gear has been rotated by 55°) from the condition of FIG. 21; in this case, the driven gear 40 has been rotated by about 36°. When the roller 61 (driving gear 12) is rotated further by about 40° from the condition shown in FIG. 22 (the total rotation being 95°), the condition of FIG. 23 is established; in this case, the driven gear 40 is rotated further by about 36° from the condition of FIG. 22, with the total rotation being 72°. In addition, the driven gear turning projection 14 of the driving gear 12 is disengaged from the first turning groove 44a of the driven gear 40. When the roller 61 (driving gear 12) is rotated further by about 265° from the condition of FIG. 23 (the total rotation being about 360°: one revolution), the condition of FIG. 24 is established. The rotation of the roller 61 in this instance does not effect rotation of the driven gear 40. In this position, the driven gear turning projection 14 of the driving gear 12 is located in the vicinity of the second turning groove 44b of the driven gear 40. When the roller 61 (driving gear 12) is rotated further by about 95° from the condition of FIG. 24 (the total rotation being about 455°), the driven gear turning projection 14 of the driving gear 12 enters into the second turning groove 44b of the driven gear 40, then rotates the driven gear 40, and is thereafter disengaged from the second turning groove 44b of the driven gear 40, resulting in the condition shown in FIG. 25. By this, the driven gear 40 is rotated by about 72° (the total rotation being 144°). When the roller 61 (driving gear 12) is rotated further by about 360° from the condition of FIG. 25 (the total rotation being about 815°: a little more than two revolutions), the driven gear turning projection 14 of the driving gear 12 enters into the third turning groove 44c of the driven gear 40, then rotates the driven gear 40, and is thereafter disengaged from the third turning groove 44c of the driven gear 40, resulting in the condition shown in FIG. 26. By this, the driven gear 40 is rotated by about 72° (the total rotation being 216°). When the roller 61 (driving gear 12) is rotated by about 360° from the condition of FIG. 26 (the total rotation being about 1175°: a little more than three revolutions), the driven gear turning projection 14 of the driving gear 12 enters into the fourth turning groove 44d of the driven gear 40, then rotates the driven gear 40, and is thereafter disengaged from the fourth turning groove 44d of the driven gear 40, resulting in the condition shown in FIG. 27. By this, the driven gear 40 is rotated by about 72° (the total rotation being 288°). When the roller is turned by about 270° from the condition of FIG. 27 (the total rotation being 1475°), the condition of FIG. 28 is obtained. When it is attempted to rotate the roller 61 (driving gear 12) further from the condition of FIG. 28, the driven gear turning projection 14 of the driving gear 12 is engaged with (makes contact with) the stopping recess portion 43 of the driven gear 40, thereby inhibiting the roller 61 from rotating further; thus, a condition is established wherein a stopper function is working. Therefore, in this embodiment, the stopper function of the Geneva gear mechanism operates in the condition wherein the roller 61 has been rotated by about 1175° (a little more than three revolutions).

In this Geneva gear mechanism, the driving gear 12 provided on the roller 61 rotates the driven gear 40 intermittently, and rotational resistance on the driven gear 40 is so little that it does not increase rotational resistance on the roller 61.

The stent delivery system described here is configured so that the stopper operates after a sufficient amount of wire has been wound. The increase in the rotational resistance on the operating rotary roller due to the wire winding amount restriction mechanism and the stopper function is relatively little and so the operationality of the operating rotary roller is favorable. In addition, the wire winding amount restriction mechanism avoids needless curving or damage of a catheter due to excessive winding of the wire by which the tubular member serving as a restraint body for the stent is pulled proximally.

The operating section functions after winding of a wire by a sufficient amount and permits quite good wire winding by the operating rotary roller, without increasing in the rotational resistance on the operating rotary roller.

The detailed description above describes features and aspects of an embodiment of a stent delivery system disclosed by way of example. The invention is not limited, however, to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A stent delivery system comprising:
a tube body having a guide wire lumen;
a stent-containing tubular member enveloping a distal end portion of the tube body and being slidable relative to the tube body toward a proximal end of the tube body;
a stent contained in the stent-containing tubular member;
a wire having one end portion fixed to the stent-containing tubular member and operable to move the stent-containing tubular member in a proximal direction;
the tube body including a stent lock section abutting a proximal end of the stent contained in the stent-containing tubular member to restrict movement of the stent in the proximal direction;
the stent possessing a cylindrical shape and being contained in the stent-containing tubular member while in a compressed state in which the stent is compressed toward a center axis of the stent, and the stent being restored to a pre-compression shape through outward expansion when indwelled in a living body;
an operating section located proximally of the stent-containing tubular member;
the operating section including a wire winding mechanism for winding the wire to thereby move the stent-containing tubular member toward the proximal direction and a wire winding amount restriction mechanism for restricting a length of the wire pulled by the wire winding mechanism;
the wire winding mechanism including an operating section housing and an operating rotary roller having a portion exposed from the operating section housing which is operable by a user to rotate the operating rotary roller and wind the wire;
the wire winding mechanism including a winding shaft section coaxial and integral with the operating rotary roller, the one end portion of the wire being held on the winding shaft section;
the winding shaft section having a smaller outer diameter than the operating rotary roller;
the wire winding amount restriction mechanism including a driving gear coaxial and integral with the operating rotary roller and a driven gear rotated intermittently by the driving gear; and
the driven gear and the driving gear being configured as a stopper to stop rotation of the driving gear after rotation of the driving gear by a predetermined amount;
wherein:
the driven gear includes a centrally located rotary shaft by which the driven gear is rotatably mounted, and a plurality of turning grooves extending a first predetermined length from a circumference of the driven gear toward the rotary shaft, and one stopping recess, the turning grooves and the one stopping recess lying in a common axial plane and being spaced apart from one another along a circumference of the driven gear;
the driving gear includes a driven gear turning projection movable into and out of the turning grooves, one-by-one, during successive rotations of the driving gear to rotate the driven gear, and engageable with the one stopping recess; and
the stopping recess extending from the circumference of the driven gear toward the rotary shaft a second predetermined length, said second predetermined length being less than the first predetermined length such that a bottom surface of the stopping recess is spaced a greater distance from the rotary shaft than a bottom surface of each of the turning grooves.

2. The stent delivery system according to claim 1, wherein:
an outer edge of the driven gear includes outer edge portions extending between the turning grooves and the stopping recess, the outer edge portions being configured as commonly configured arcuate recesses; and
the driving gear has an arcuate rib possessing an outer surface shape corresponding to each of the arcuate recesses of the driven gear, the arcuate rib on the driving gear successively contacting the outer edge portions of the driven gear during successive rotations of the driving gear.

3. The stent delivery system according to claim 2, wherein the arcuate rib is a circular surface which possesses a radius of curvature, and including a rib-missing portion devoid of the arcuate rib, the rib-missing section also possessing said radius of curvature, the rib-missing section being positioned in radial alignment with the driven gear turning projection.

4. The stent delivery system according to claim 1, wherein the driving gear and the winding shaft section are located on opposite axial sides of the rotary roller.

5. The stent delivery system according to claim 1, wherein the operating section housing includes a shaft-forming projection forming a rotary shaft for the driven gear, and the driven gear includes a bearing section for receiving the shaft-forming projection.

6. The stent delivery system according to claim 1, wherein an inner surface of the operating section housing includes a recess in which is positioned the driven gear and the driven gear turning projection.

7. The stent delivery system according to claim 1, wherein the operating section housing includes a driven gear containing section in which is positioned the driven gear, and wherein the driven gear and the driven gear containing section are each provided with a through-hole.

8. The stent delivery system according to claim 1, wherein the driving gear possesses an outer diameter smaller than an outer diameter of the operating rotary roller.

9. The stent delivery system according to claim 1, wherein the operating section includes a lock for releasably locking rotation of the wire winding mechanism.

10. The stent delivery system according to claim 1, wherein the operating section has a reverse rotation restriction mechanism for restricting rotation of the wire winding mechanism in a reverse direction relative to a winding direction in which the wire is wound on the winding shaft section.

11. The stent delivery system according to claim 1, wherein the wire winding mechanism includes a collar section enveloping the winding shaft section so that an annular space exists between an inner surface of the collar section and an outer surface of the winding shaft section, the collar section restraining loosening of the wire wound onto the winding shaft section.

12. The stent delivery system according to claim 1, wherein the driving gear and the driven gear constitute a Geneva gear mechanism.

13. The stent delivery system according to claim 1, wherein the tube body includes a distal-side tube having a guide wire lumen, and a proximal-side tube fixed to the distal-side tube so that the distal-side tube is positioned distally of the proximal-side tube, the stent-containing tubular member surrounding a distal end portion of the distal-side tube and being slidable toward a proximal end of the distal-side tube, the wire extending inside the proximal-side tube, and the distal-side tube containing the stent lock section.

14. The stent delivery system according to claim 13, further comprising a fixed tube to which a proximal portion of the distal-side tube and a distal portion of the proximal-side tube are fixed, the fixed tube having an opening communicating with the guide wire lumen.

15. The stent delivery system according to claim 14, further comprising:
 a slide tube adjacent a proximal end of the stent-containing tubular member and slidable in the proximal direction;
 the fixed tube being positioned to slidably receive a proximal portion of the slide tube;
 the slide tube being slidable toward the proximal direction together with the stent-containing tubular member by winding the wire, the slide tube not being fixed to the stent-containing tubular member;
 the slide tube including a slide tube body and a distal-side tubular member fixed to a distal end portion of the slide tube body, the distal-side tubular member covering a distal end of the slide tube body and extending distally beyond a distal-most end of the slide tube body; and
 the distal-side tubular member is a one-piece unitary tubular body having a reduced-diameter section located between a distal end and a proximal end of the distal-side tubular member and possessing at least an inside diameter that is reduced relative to the inside diameter of portions of the distal-side tubular member on opposite sides of the reduced-diameter section.

16. A stent delivery system comprising:
 a tube body having a guide wire lumen for receiving a guide wire to guide movement of the stent delivery system;
 a stent-containing tubular member surrounding a portion of the tube body and axially movable relative to the tube body;
 a compressed stent positioned in the stent-containing tubular member, the compressed stent expanding to a non-compressed state when removed from the stent-containing tubular member and indwelled in a living body;
 a wire having one end portion fixed to the stent-containing tubular member, the wire also possessing an opposite end portion;
 a rotary roller rotatably mounted in a housing and rotatably operable from outside the housing to rotate the operating rotary roller;
 a winding shaft coaxial with the rotary roller and fixed to the rotary roller to rotate together with the rotary roller, the opposite end portion of the wire being held on the winding shaft so that the wire is wound on the winding shaft during rotation of the rotary roller in one rotational direction to move the stent-containing tubular member proximally to allow the stent to be removed from the stent-containing tubular member;
 a driving gear coaxial and integral with the rotary roller to rotate with the rotary roller about a first rotation axis, the driving gear including an engaging portion which rotates together with the driving gear;
 a driven gear positioned adjacent the driving gear and rotatable about a second rotation axis non-coaxially arranged relative to the first rotation axis;
 the engaging portion of the driving gear engaging the driven gear during rotation of the driving gear to cause the driven gear to rotate; and
 the driven gear including a stop portion engageable by the engaging portion of the driving gear after the driving gear has rotated a predetermined amount so that further rotation of the driving gear is stopped when the engaging portion engages the stop, the predetermined amount of rotation of the driving gear being an amount that winds a portion of the wire on the winding shaft so that the stent-containing tubular member is moved proximally to allow the stent to be removed from the stent-containing tubular member;
 wherein the driven gear is rotatably mounted about a centrally located rotary shaft, the driven gear includes a plurality of turning grooves extending a first predetermined length radially inwardly from an outer periphery of the driven gear and opening to the outer periphery of the driven gear, the engaging portion of the driving gear being a projection extending away from the driving gear, the stop portion being a stopping recess formed in the outer periphery of the driven gear and extending a second predetermined length radially inwardly from the outer periphery of the driven gear, the turning grooves and the stopping recess being spaced apart from one another along the outer periphery of the driven gear, said second predetermined length being less than the first predetermined length such that a bottom surface of the stopping recess is spaced a greater distance from the rotary shaft than a bottom surface of each of the turning grooves.

17. The stent delivery system according to claim 16, wherein:
 the outer periphery of the driven gear includes a plurality of outer peripheral portions each extending between adjacent turning grooves, each of the outer peripheral portions being commonly shaped as an arcuate recess; and
 the driving gear has an arcuate rib possessing an outer surface shape corresponding to the shape of the arcuate recesses of the driven gear, the arcuate rib on the driving gear successively contacting the outer peripheral portions of the driven gear during successive rotations of the driving gear.

18. The stent delivery system according to claim 1, wherein the turning grooves and the stopping recess are at equal angular intervals around the rotary shaft.

19. The stent delivery system according to claim 16, wherein the turning grooves and the stopping recess are at equal angular intervals around the rotary shaft.

* * * * *